United States Patent
Xiao et al.

(10) Patent No.: US 10,758,303 B2
(45) Date of Patent: *Sep. 1, 2020

(54) HOLLOW BODY CAVITY ABLATION APPARATUS

(71) Applicant: CARDEA MEDSYSTEMS (TIANJIN) CO., LTD., Nankai District (CN)

(72) Inventors: Jia Hua Xiao, Santa Rosa, CA (US); Roger A. Stern, Cupertino, CA (US); Jerome Jackson, Los Altos, CA (US); Grant Michael Glaze, Sunnyvale, CA (US)

(73) Assignee: CARDEA MEDSYSTEMS (TIANJIN) CO., LTD., Nankai District (CN)

( * ) Notice: Subject to any disclaimer, the term of this patent is extended or adjusted under 35 U.S.C. 154(b) by 756 days.

This patent is subject to a terminal disclaimer.

(21) Appl. No.: 14/736,212

(22) Filed: Jun. 10, 2015

(65) Prior Publication Data
US 2015/0272670 A1  Oct. 1, 2015

Related U.S. Application Data

(63) Continuation of application No. 12/927,311, filed on Nov. 10, 2010, now Pat. No. 9,173,702.
(Continued)

(51) Int. Cl.
*A61B 18/12* (2006.01)
*A61B 18/14* (2006.01)
(Continued)

(52) U.S. Cl.
CPC ...... *A61B 18/1492* (2013.01); *A61B 18/1485* (2013.01); *A61M 25/0136* (2013.01);
(Continued)

(58) Field of Classification Search
CPC ............ A61B 2018/1465; A61B 18/14; A61B 18/148; A61B 18/1482; A61B 18/1485;
(Continued)

(56) References Cited

U.S. PATENT DOCUMENTS 3,924,628 A    12/1975  Droegemueller et al.
4,016,867 A     4/1977  King et al.
(Continued)

FOREIGN PATENT DOCUMENTS

CN    1290148 A    4/2001
CN    1308510 A    8/2001
(Continued)

OTHER PUBLICATIONS

Novasure: Instructions for Use and Controller Operator's Manual, Cytyc Surgical Products, 2004, 716011 Revision B.
(Continued)

*Primary Examiner* — Jaymi E Della
(74) *Attorney, Agent, or Firm* — Jennifer A. Haynes; David Lewis

(57) ABSTRACT

An ablation apparatus places electrodes at the perimeter of a cavity. In an embodiment, the alternating electric field is used to expose the cavity to enough energy to ablate the cavity. In an embodiment, two modes are used to expose different regions of the cavity to different amounts of power for so that the thermal effect is more uniform. In an embodiment, the electrodes have a relatively large surface area so as to avoid charring the cavity, but are shaped so as to fit within a body orifice. For example, the diameter of the sheathed housing the electrodes during penetration may be only 5.5 mm.

37 Claims, 23 Drawing Sheets

Related U.S. Application Data

(60) Provisional application No. 61/259,973, filed on Nov. 10, 2009.

(51) Int. Cl.
*A61M 25/01* (2006.01)
*A61B 18/00* (2006.01)

(52) U.S. Cl.
CPC ..... *A61M 25/0147* (2013.01); *A61B 18/1206* (2013.01); *A61B 2018/00011* (2013.01); *A61B 2018/0016* (2013.01); *A61B 2018/00083* (2013.01); *A61B 2018/00214* (2013.01); *A61B 2018/00267* (2013.01); *A61B 2018/00482* (2013.01); *A61B 2018/00559* (2013.01); *A61B 2018/00577* (2013.01); *A61B 2018/00684* (2013.01); *A61B 2018/00916* (2013.01); *A61B 2018/144* (2013.01); *A61B 2018/1407* (2013.01); *A61B 2018/1437* (2013.01); *A61B 2018/1465* (2013.01); *A61B 2018/1467* (2013.01); *A61B 2018/1475* (2013.01); *A61B 2218/007* (2013.01)

(58) Field of Classification Search
CPC ........... A61B 2018/00214; A61B 2018/00267; A61B 2018/00559; A61B 2018/00654; A61B 2018/1405; A61B 2018/1407; A61B 2018/144
See application file for complete search history.

(56) References Cited

U.S. PATENT DOCUMENTS

| | | |
|---|---|---|
| 4,121,572 A | 10/1978 | Krzeminski |
| 4,204,548 A | 5/1980 | Kurz |
| 4,685,474 A | 8/1987 | Kurz et al. |
| 4,764,845 A | 8/1988 | Artus |
| 4,873,986 A | 10/1989 | Wallace |
| 4,932,421 A | 6/1990 | Kaali et al. |
| 4,949,718 A | 8/1990 | Neuwirth et al. |
| 5,242,390 A | 9/1993 | Goldrath |
| 5,275,595 A | 1/1994 | Dobak, III |
| 5,277,201 A * | 1/1994 | Stern ............... A61B 18/14 606/32 |
| 5,313,943 A * | 5/1994 | Houser ............... A61B 5/0422 600/374 |
| 5,437,629 A | 8/1995 | Goldrath |
| 5,449,380 A | 9/1995 | Chin |
| 5,500,012 A | 3/1996 | Brucker et al. |
| 5,520,682 A | 5/1996 | Baust et al. |
| 5,540,658 A | 7/1996 | Evans et al. |
| 5,542,928 A | 8/1996 | Evans et al. |
| 5,558,672 A | 9/1996 | Edwards et al. |
| 5,575,788 A | 11/1996 | Baker et al. |
| 5,613,950 A | 3/1997 | Yoon |
| 5,647,868 A | 7/1997 | Chinn |
| 5,693,078 A | 12/1997 | Desai et al. |
| 5,702,438 A * | 12/1997 | Avitall ............... A61B 18/1492 600/374 |
| 5,769,880 A | 6/1998 | Truckai et al. |
| 5,776,129 A | 7/1998 | Mersch |
| 5,782,899 A | 7/1998 | Imran |
| 5,800,493 A | 9/1998 | Stevens et al. |
| 5,848,969 A | 12/1998 | Panescu et al. |
| 5,868,735 A | 2/1999 | Lafontaine |
| 5,868,740 A | 2/1999 | LeVeen et al. |
| 5,891,134 A | 4/1999 | Goble et al. |
| 5,916,213 A | 6/1999 | Haissaguerre et al. |
| 5,954,714 A * | 9/1999 | Saadat ............... A61B 18/08 606/28 |
| 6,009,877 A | 1/2000 | Edwards |
| 6,033,397 A | 3/2000 | Laufer et al. |
| 6,033,398 A | 3/2000 | Farley et al. |
| 6,068,629 A | 5/2000 | Haissaguerre et al. |
| 6,139,538 A | 10/2000 | Houghton et al. |
| 6,142,994 A * | 11/2000 | Swanson ............ A61B 18/1482 606/41 |
| 6,161,047 A | 12/2000 | King et al. |
| 6,197,022 B1 | 3/2001 | Baker |
| 6,270,495 B1 | 8/2001 | Palermo |
| 6,306,129 B1 | 10/2001 | Little et al. |
| 6,425,895 B1 | 7/2002 | Swanson et al. |
| 6,475,212 B2 | 11/2002 | Dobak, III et al. |
| 6,514,252 B2 | 2/2003 | Nezhat et al. |
| 6,547,784 B1 | 4/2003 | Thompson et al. |
| 6,620,161 B2 | 9/2003 | Schulze et al. |
| 6,813,520 B2 | 11/2004 | Truckai et al. |
| 6,929,642 B2 | 8/2005 | Xiao et al. |
| 6,960,203 B2 | 11/2005 | Xiao et al. |
| 7,074,217 B2 | 7/2006 | Strul et al. |
| 7,101,367 B2 | 9/2006 | Xiao et al. |
| 7,115,124 B1 | 10/2006 | Xiao |
| 7,481,808 B2 | 1/2009 | Koyfman et al. |
| 9,173,702 B2 | 11/2015 | Stern et al. |
| 2002/0022870 A1 | 2/2002 | Truckai et al. |
| 2002/0111615 A1 | 8/2002 | Cosman et al. |
| 2002/0120261 A1 | 8/2002 | Morris et al. |
| 2002/0151889 A1 | 10/2002 | Swanson et al. |
| 2003/0199817 A1* | 10/2003 | Thompson ......... A61B 18/1492 604/95.01 |
| 2003/0212389 A1 | 11/2003 | Durgin et al. |
| 2004/0002698 A1 | 1/2004 | Hua Xiao et al. |
| 2004/0002702 A1 | 1/2004 | Xiao et al. |
| 2004/0002703 A1* | 1/2004 | Xiao ................... A61B 18/1485 606/41 |
| 2004/0054366 A1 | 3/2004 | Davison et al. |
| 2005/0033285 A1 | 2/2005 | Swanson et al. |
| 2005/0267468 A1* | 12/2005 | Truckai .............. A61B 18/1485 606/41 |
| 2006/0089636 A1* | 4/2006 | Christopherson .. A61B 18/1485 606/41 |
| 2007/0083193 A1 | 4/2007 | Werneth et al. |
| 2007/0083195 A1* | 4/2007 | Werneth ............ A61B 18/1492 606/41 |
| 2007/0270796 A2* | 11/2007 | Girard .................. A61B 18/14 606/45 |
| 2009/0054773 A1 | 2/2009 | Shizuka |
| 2009/0062787 A1 | 3/2009 | Schaer et al. |
| 2009/0062795 A1 | 3/2009 | Vakharia et al. |
| 2011/0112524 A1 | 5/2011 | Stern et al. |
| 2015/0305805 A1 | 10/2015 | Xiao et al. |

FOREIGN PATENT DOCUMENTS

| | | |
|---|---|---|
| CN | 100396251 C | 6/2008 |
| CN | 102256560 A | 11/2011 |
| CN | 102596082 A | 7/2012 |
| CN | 102596082 B | 2/2015 |
| EP | 2498708 | 9/2012 |
| WO | WO/1995/10326 | 4/1995 |
| WO | WO 2011/059487 | 5/2011 |

OTHER PUBLICATIONS

Picture of Novasure Unit, Unit with Disposable, and Novasure Disposable (from prior to Aug. 10, 2010).

Title: "Treatment of Menorrhagia by Radio Frequency Heating"; Prior, M. V., et al., vol. 7, No. 2, International Journal of Hyperthermia, Taylor & Francis Ltd.; Year: 1991, pp. 213-220.

Title: "Cryocoagulation of the Endometrium at the Uterine Cornua"; Droegemueller, William, et al., vol. 131, No. 1, American Journal of Obstetrics and Gynecology; The C. V. Mosby Co.; Year: May 1, 1978, pp. 1-9.

Title: "A Computer-Controlled, Continuously Circulating, Hot Irrigating System for Endometrial Ablation"; Baggish, Michael, et al., vol. 173, No. 6, American Journal of Obstetrics and Gynecology; The C. V. Mosby Co.; Year: Dec. 1995, pp. 1842-1848.

(56) References Cited

OTHER PUBLICATIONS

Title: "Preliminary Clinical Experience With a Thermal Balloon Endometrial Ablation Method to Treat Menorrhagia"; Singer, Albert, et al., vol. 83, No. 5, Part 1, The American College of Obstetricians and Gynecologists; Year: May 1994, pp. 732-734.

* cited by examiner

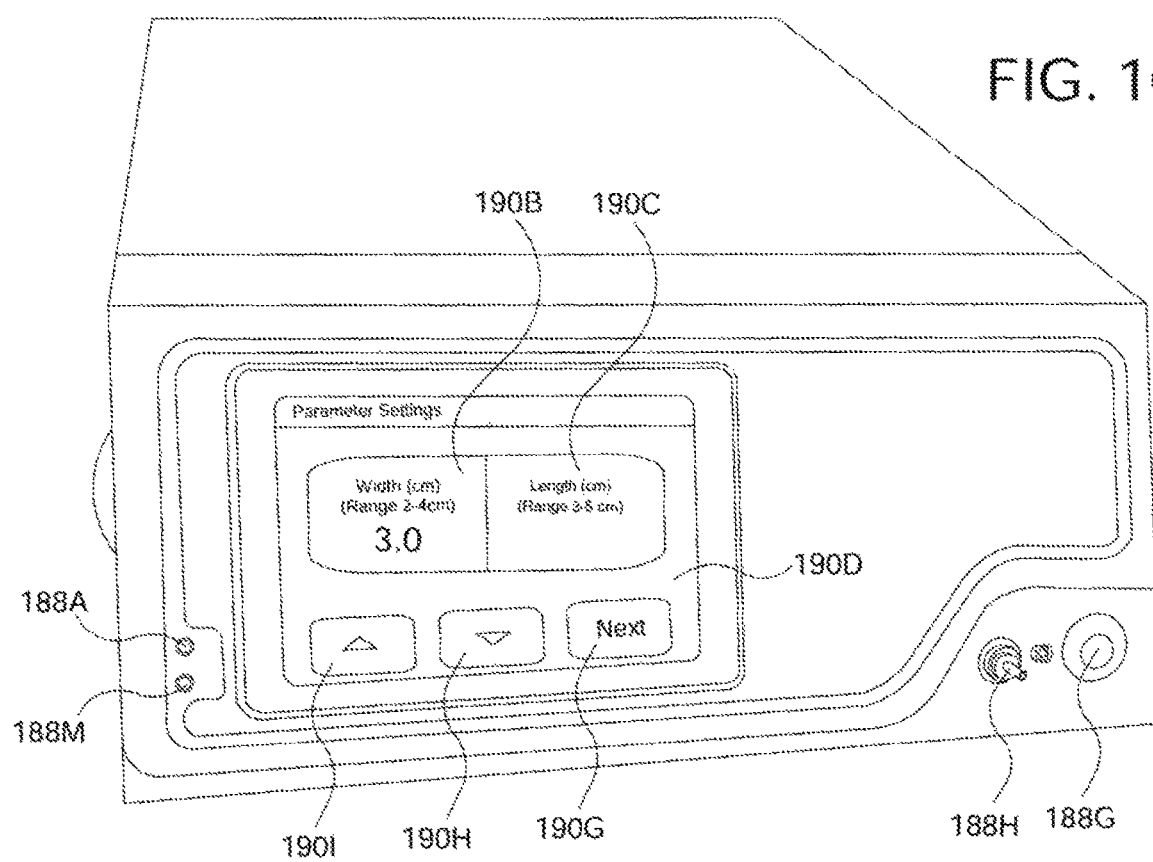

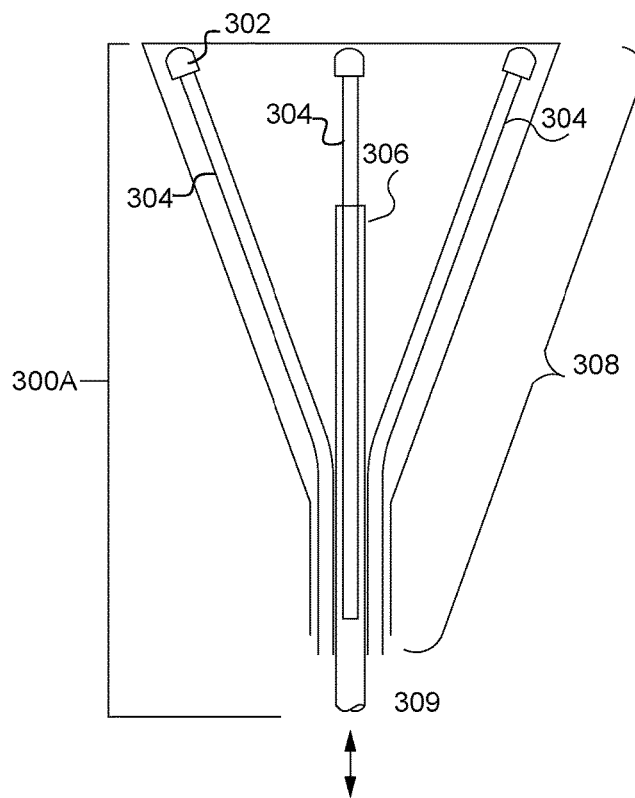
FIG. 3A
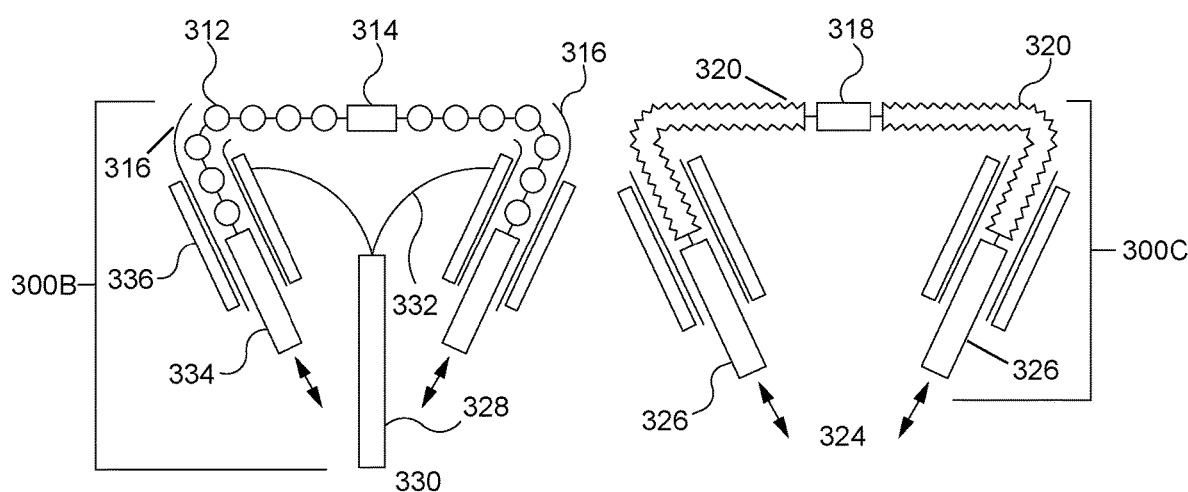
FIG. 3B
FIG. 3C

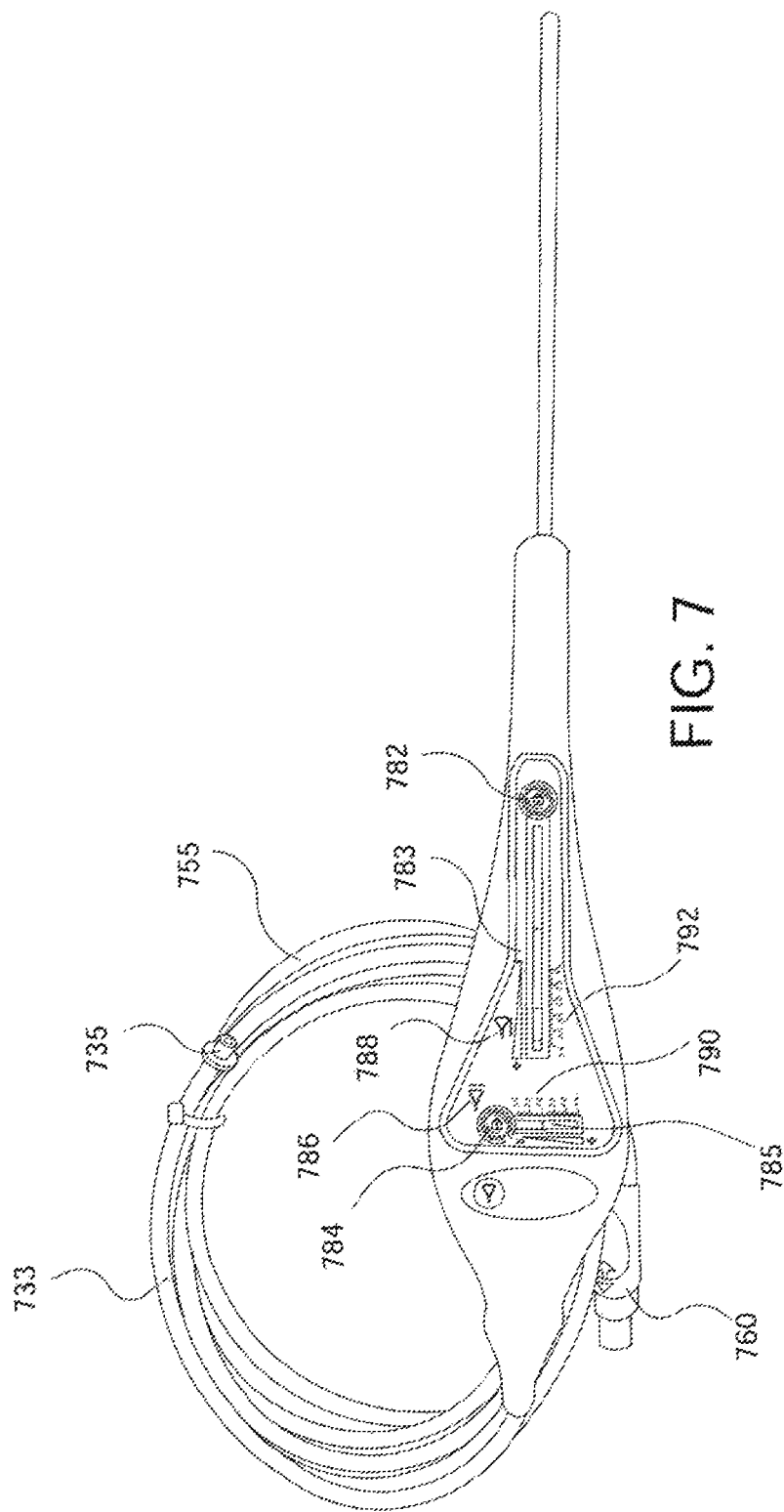

Table 2A FIG. 16

| Treatment # | Dimensions | | Phase | | | | Depth (mm) | | |
|---|---|---|---|---|---|---|---|---|---|
| | | | Mode 1 | | Mode 2 | | | | |
| | Width (cm) | Length (cm) | Power (W) | Time (s) | Power (W) | Time (s) | D1 - Proximal | D2 - Half | D3 - Center |
| 1 | 3.25 | 5.25 | 75 | 90 | 35 | 30 | 5 | 7 | 6 |
| 2 | 3.25 | 5.25 | 75 | 90 | 35 | 30 | 5 | 8 | 7 |
| 3 | 3.25 | 5.25 | 75 | 90 | 35 | 30 | 6 | 6 | 7 |
| 4 | 3.25 | 5.25 | 75 | 90 | 35 | 30 | 5 | 6 | 5 |
| 5 | 3.25 | 4 | 70 | 90 | 20 | 30 | 5 | 7 | 6 |
| 6 | 3.25 | 4 | 70 | 90 | 20 | 30 | 5 | 7 | 6 |
| 7 | 3.25 | 4 | 70 | 90 | 20 | 30 | 5 | 8 | 7 |
| 8 | 3.25 | 4 | 70 | 90 | 20 | 30 | 5 | 7 | 6 |
| 2 | 4.5 | 6.5 | 100 | 120 | 50 | 30 | 5 | 7 | 6 |
| 3 | 4.5 | 6.5 | 100 | 120 | 50 | 30 | 5 | 6 | 7 |
| 4 | 4.5 | 6.5 | 100 | 120 | 50 | 30 | 5 | 8 | 7 |
| 5 | 4.5 | 6.5 | 100 | 120 | 50 | 30 | 5 | 7 | 7 |
| 6 | 4.5 | 6.5 | 100 | 120 | 50 | 30 | 5 | 8 | 10 |
| 7 | 4.5 | 6.5 | 100 | 120 | 60 | 30 | 5 | 8 | 7 |
| 8 | 3.25 | 6.5 | 85 | 90 | 50 | 30 | 5 | 7 | 7 |
| 9 | 3.25 | 6.5 | 85 | 90 | 50 | 30 | 5 | 7 | 7 |
| 10 | 3.25 | 6.5 | 85 | 90 | 50 | 30 | 5 | 8 | 6 |
| 12 | 3.25 | 6.5 | 85 | 90 | 50 | 30 | 5 | 6 | 7 |
| 13 | 3.25 | 6.5 | 85 | 90 | 70 | 30 | 5 | 5 | 7 |
| 14 | 2 | 6.5 | 80 | 60 | 55 | 30 | 5 | 6 | 7 |
| 15 | 2 | 6.5 | 80 | 60 | 55 | 30 | 5 | 5 | 6 |
| 16 | 2 | 6.5 | 80 | 60 | 55 | 30 | 5 | 6 | 6 |
| 17 | 2 | 6.5 | 80 | 60 | 75 | 30 | 5 | 5 | 5 |
| 18 | 2 | 6.5 | 80 | 90 | 75 | 30 | 5 | 6 | 7 |
| 19 | 2 | 6.5 | 80 | 90 | 55 | 30 | 5 | 5 | 8 |
| 20 | 2 | 6.5 | 80 | 90 | 55 | 30 | 5 | 6 | 8 |

Table 2B FIG. 17

| Treatment | Dimensions | | Phase | | | | Half D3/D5 - Distal | Result |
| --- | --- | --- | --- | --- | --- | --- | --- | --- |
| | Width (cm) | Length (cm) | Mode 1 | | Mode 2 | | | |
| | | | Power (W) | Time (s) | Power (W) | Time (s) | | |
| 1 | 3.25 | 5.25 | 75 | 90 | 35 | 30 | 6 / 5 | Good |
| 2 | 3.25 | 5.25 | 75 | 90 | 35 | 30 | 6 / 5 | Good |
| 3 | 3.25 | 5.25 | 75 | 90 | 35 | 30 | 7 / 5 | Good |
| 4 | 3.25 | 5.25 | 75 | 90 | 35 | 30 | 6 / 5 | Good |
| 5 | 3.25 | 4 | 70 | 90 | 20 | 30 | 6 / 5 | Good |
| 6 | 3.25 | 4 | 70 | 90 | 20 | 30 | 5 / 6 | Good |
| 7 | 3.25 | 4 | 70 | 90 | 20 | 30 | 6 / 5 | Good |
| 8 | 3.25 | 4 | 70 | 90 | 20 | 30 | 6 / 5 | Good |
| 2 | 4.5 | 6.5 | 100 | 120 | 50 | 30 | 7 / 5 | Good |
| 3 | 4.5 | 6.5 | 100 | 120 | 50 | 30 | 7 / 5 | Good |
| 4 | 4.5 | 6.5 | 100 | 120 | 50 | 30 | 8 / 7 | Good |
| 5 | 4.5 | 6.5 | 100 | 120 | 50 | 30 | 8 / 6 | Good |
| 6 | 4.5 | 6.5 | 100 | 120 | 50 | 30 | 7 / 6 | Good |
| 7 | 4.5 | 6.5 | 100 | 120 | 60 | 30 | 10 / 8 | Good |
| 8 | 3.25 | 6.5 | 85 | 90 | 50 | 30 | 7 / 5 | Good |
| 9 | 3.25 | 6.5 | 85 | 90 | 50 | 30 | 8 / 5 | Good |
| 10 | 3.25 | 6.5 | 85 | 90 | 50 | 30 | 7 / 5 | Good |
| 11 | 3.25 | 6.5 | 85 | 90 | 50 | 30 | 6 / 6 | Good |
| 12 | 3.25 | 6.5 | 85 | 90 | 70 | 30 | 7 / 5 | Good |
| 13 | 3.25 | 6.5 | 80 | 60 | 55 | 30 | 6 / 5 | Good |
| 14 | 2 | 6.5 | 80 | 60 | 55 | 30 | 6 / 6 | Good |
| 15 | 2 | 6.5 | 80 | 60 | 55 | 30 | 5 / 5 | Good |
| 16 | 2 | 6.5 | 80 | 60 | 75 | 30 | 7 / 5 | Good |
| 17 | 2 | 6.5 | 80 | 90 | 75 | 30 | 7 / 6 | Good |
| 18 | 2 | 6.5 | 80 | 90 | 55 | 30 | 7 / 5 | Good |
| 19 | 2 | 6.5 | 80 | 90 | 55 | 30 | 7 / 6 | Good |
| 20 | 2 | 6.5 | 80 | 90 | 55 | 30 | 7 / 5 | Good |

HOLLOW BODY CAVITY ABLATION APPARATUS

CROSS-REFERENCE TO RELATED APPLICATIONS

This application is also a continuation of U.S. patent application Ser. No. 12/927,311, now U.S. Pat. No. 9,173,702, entitled "Hollow body cavity ablation device," filed on Nov. 10, 2010, by Roger Allan Stern; which claims priority benefit of U.S. Provisional Patent Application No. 61/259,973, entitled "Hollow Body Cavity Ablation Apparatus," filed Nov. 10, 2009. All of the above patent applications are incorporated herein by reference.

FIELD

This specification generally relates to embodiments of hollow body ablation devices and uses thereof.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Ablation of the interior lining of a body organ is a procedure that involves heating the organ lining to temperatures that destroys the cells of the lining and coagulates blood flow for hemostasis. Such a procedure may be performed as a treatment to one of many conditions, such as chronic bleeding of the endometrial layer of the uterus or abnormalities of the mucosal layer of the gallbladder. Existing methods for effecting ablation include circulation of a heated fluid inside the organ (either directly or inside a balloon) and laser treatment of the organ lining. New methods and devices may be desirable for effecting hollow body cavity ablation.

SUMMARY

Methods and devices are provided for effecting hollow body cavity ablation. The devices are adjustable to fit the perimeter of a variety of organ sizes and to fold into a small size for insertion into a small opening.

Any of the above embodiments may be used alone or together with one another in any combination. Inventions encompassed within this specification may also include embodiments that are only partially mentioned or alluded to or are not mentioned or alluded to at all in this brief summary or in the abstract.

BRIEF DESCRIPTION OF THE FIGURES

In the following drawings like reference numbers are used to refer to like elements. Although the following figures depict various examples of the invention, the invention is not limited to the examples depicted in the figures.

FIG. 1C shows a screen shot of another screen of a user interface of the controller system.

FIGS. 3A-C show front elevation views of three more embodiments of hollow body ablation devices. FIG. 3B is a partial cutaway view of an embodiment of a hollow body ablation device.

FIG. 7 shows a front elevation view of an embodiments of the outside of the handpiece on FIG. 6A, including length and width adjustments.

FIGS. 16 and 17 show Tables 2A and 2B, which show test results of the ablation.

DETAILED DESCRIPTION

Figure 1A:
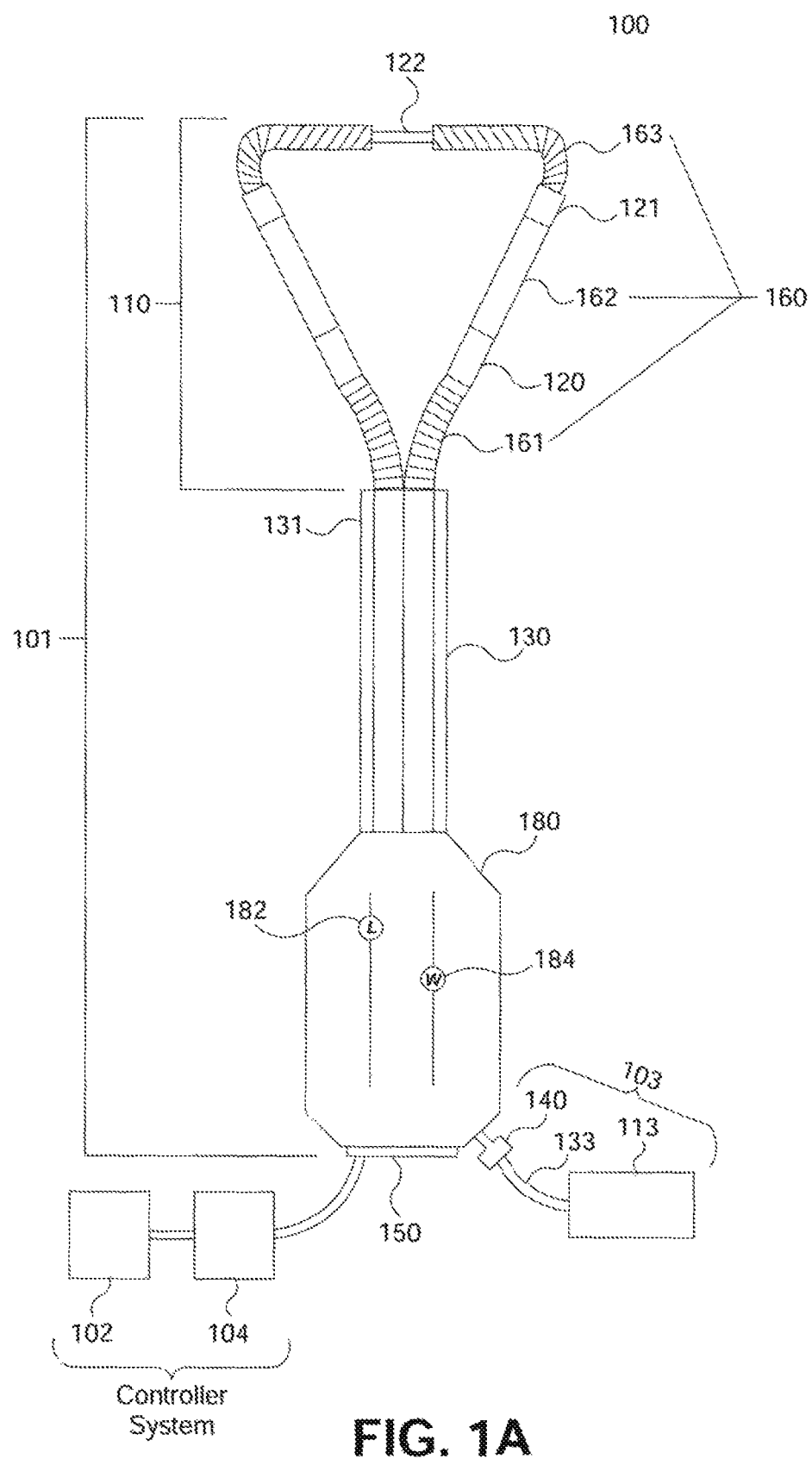
FIG. 1A shows a front elevation view of an embodiment of a hollow body ablation device attached to a controller system and a fluid removal device.

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

In general, at the beginning of the discussion of each of FIGS. 1A-8 is a brief description of each element, which may have no more than the name of each of the elements in the one of FIGS. 1A-8 that is being discussed. After the brief description of each element, each element is further discussed in numerical order. In general, each of FIGS. 1-17 is discussed in numerical order and the elements within FIGS. 1-17 are also usually discussed in numerical order to facilitate easily locating the discussion of a particular element. Nonetheless, there is no one location where all of the information of any element of FIGS. 1A-17 is necessarily located. Unique information about any particular element or any other aspect of any of FIGS. 1A-17 may be found in, or implied by, any part of the specification.

In various places in discussing the drawings a range of letters, such as "a-z" are used to refer to individual elements of various series of elements that are the same. In each of these series, the ending letters are integer variables that can be any number. Unless indicated otherwise, the number of elements in each of these series is unrelated to the number of elements in others of these series. Specifically, even though one letter (e.g. "a") comes earlier in the alphabet than another letter (e.g., "e"), the order of these letters in the alphabet does not mean that the earlier letter represents a smaller number. The value of the earlier letter is unrelated to the later letter, and may represent a value that is greater the same or less than the later letter.

FIG. 1 shows an overhead view of an embodiment of a hollow body ablation apparatus used in methods of ablation of hollow body organs. The ablation apparatus 100 may include a handheld implement 101, a power supply 102, a controller system (a controller) 104 and an aspirator device 103. The handheld implement 101 may include a head 110, a reservoir 113, a connector 150, an aspiration port 140, a sheath 130, an aspiration tube 133, one or more insulators 120, 121, and 122, one or more electrodes 160*a-z*, a handpiece 180, a length adjustment 182, a width adjustment 184 for deploying the device. Ablation apparatus 100 may also include foot control 186. In other embodiments the ablation apparatus 100 and/or handheld implement 101 may not have all of the elements or features listed and/or may have other elements or features instead of or in addition to those listed.

In this application the term "perimeter" when used in reference to the uterus refers to outside of the ablation region or endometrium. The ablation apparatus 100 is an example of a system that can be used for ablation of the interior lining of a body organ that may be hollow. The ablation apparatus 100 may include electrodes that can be arranged in a pattern that makes contact with the surface area of the cavity of the hollow body organ in close proximity to the perimeter. Energizing the electrodes can result in a complete or partial ablation of the lining of the body cavity without the necessity of moving the electrodes, even though the electrodes only make contact with the surface area of the organ in proximity to the perimeter. The user of ablation apparatus 100 may be anyone who uses the ablation apparatus 100 during a hollow body ablation procedure. Users may include doctors, surgeons, nurses, veterinarians, and any support staff that might be helping with a procedure, for example. The procedure may be done in an operating room or as an outpatient procedure, for example.

The handheld implement 101 can be used for ablation of a hollow cavity with anterior and posterior surfaces while the anterior and posterior surfaces are either separated or contacting one another. The handheld implement 101 may include a head 110, which may have any shape, according to the cavity that is intended to be ablated, and/or can be adjusted to approximate the perimeter of a hollow body organ. The handheld implement 101 can have electrodes arranged in a pattern that allow for placement in the perimeter of the hollow body organ. The handheld implement 101 has controls (e.g., on the handheld implement 101) that allow the user to reduce the overall profile and size of the handheld implement 101 to allow for minimally invasive access, to be able to better conform to organs with distorted cavity shapes. The handheld implement 101 has the advantage that handheld implement 101 is able to collapse on itself to form a small tube that will fit into a small diameter aperture. In some embodiments, the aperture has a diameter between about 4 and about 7 mm, including but not limited to 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, and 6.9 mm. In the case where the diameter is between 4 and 7 mm, the handheld implement 101 can collapse upon itself until handheld implement 101 has a diameter of between about 4 or 5.5 and about 7 mm, including but not limited to 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, and 6.9 mm. In some embodiments, the diameter of the aperture is about 5.5 mm and the diameter of the handheld implement 101 when collapsed is less than 5.5 mm, which is smaller than the diameter of heads of prior art ablation devices.

The handheld implement 101 in the invention can have various geometric adjustments applied through operating controls on the handpiece 180 of the handheld implement 101 that change the size and/or shape of head.

The power supply 102 may include a transformer for converting the voltage and/or an alternating current source, such as a variable oscillator, which may generate Radio Frequency (RF) Alternating Current (AC). Alternatively, power supply 102 may include a generator. The power supply 102 controls the frequency of the alternating current that is output by power supply 102.

The aspiration device 103 includes an aspiration tube 133 and a reservoir 113 and may act to remove excess fluid, (i.e. liquid, vapor and gases), from the hollow body organ before, during and/or after the process of ablation (e.g., the procedure) (it is not necessary to remove all fluids from the cavity). The aspirator device 103 can use any method of fluid removal, including a pump, suction, and/or aspirator to remove the fluids.

The controller 104 may include an algorithm that allows for the control of the alternating current (AC). The power supply 102 may be a part of the controller 104 or separate from the controller 104. The controller 104 may be capable of applying different patterns of alternating the polarities of the different electrodes of ablation apparatus 100, changing electrode polarities in various combinations to effect bipolar ablation between selected electrodes or monopolar ablation to a neutral electrode. The frequency, voltage, and/or current may be adjusted to fit the cavity dimensions to limit the ablation effects to the desired tissue or tissue layers, and minimize collateral effects, and can be used to determine overall therapeutic energy doses, and/or determine other settings such as power, duration (the amount of time) of application of the electric field, etc. See FIG. 1D for a diagram of electrode bipolar coupling pairs and FIGS. 16 and 17 for the energy delivery algorithms that can be used.

The power supply 102 and controller 104 are capable of driving multiple electrodes in various bipolar pairs located in the handheld implement 101 and in proximity to the perimeter of the hollow organ, so as to automatically sequence through a desired set of bipolar or monopolar ablation polarities and/or algorithms. The controller 104 is discussed in more detail in conjunction with reference to FIG. 2.

In some embodiments, the head 110 is a generally triangular handheld implement 101 having an approximately isosceles triangular shape. The area distal to the handpiece 180 is the base. However, even when the head 110 is a parallelogram shape, the base can still be thought of as the side distal to the handpiece 180. If the head 110 has a more circular or oval shape, the base can be thought of as the area most distal to the handpiece 180. Upon full opening of the head 110, the base can be between about 2 and about 4.5 cm and the length upon full opening of the head 110 between about 4 and about 6.5 cm. Other embodiments of this device can have generally larger or smaller base width and length ranges, depending on the size of the organ being ablated. The term generally triangular, means that the handheld implement 101 can be any shape that is generally triangular shape (including a rounded triangle). Other examples of shapes that the head may have are a square, a parallelogram, a circle, ellipse, rhombus, spiral, etc. but, in the case of the square, parallelogram, circle or ellipse. The "base" is the side most distal from the handpiece and the "sides" are the pieces on either side of the "base." The shape may depend in part on how far apart the sides are in the sheath 130 and/or handpiece 180. In some embodiments, the base is the most distal side from the handheld implement 101 and upon full opening of the handheld implement 101, the base can be between about 1.5 or 2 and about 5 cm, including but not limited to 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, and 4.9 cm. In some embodiments, the sides of the device are between about 3.5 and about 7 cm, including, but not limited to, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, and 6.9 cm.

The reservoir 113 may be a part of aspirator device 103, and may be any type of reservoir that may contain body fluids (i.e. liquids, vapors or gases) without spreading biohazards. In some embodiments. The pump, 214 in FIG. 2, can be any pump. In some embodiments, the pump is a mechanical pump, a finger pump, a syringe pump, vacuum canister, turbine pump, peristaltic pump or other method for creating a negative pressure. Alternatively, the system can be connected to wall vacuum that exists in the hospital or surgical suite.

In the embodiment shown in FIG. 1A, there are multiple insulators 120, 121, and 122 that function to keep the electrodes 160*a-z* from touching and possibly shorting out. The electrode shells may be continuous, or slotted on one or more sides or in a generally spiral pattern to facilitate bending and adaptation to the organ perimeter. The side insulators 120, 121 and 122 walls may be continuous, or slotted on one or more sides or in a generally spiral pattern to facilitate bending and adaptation to the organ perimeter. The electrode cross sections may be of any geometry, including circular, elliptical, rectangular, or nonsymmetric 'D' shaped which may be preferable for maximizing electrode surface area for contact with the organ wall for a device which must be introduced through a small diameter aperture. Similarly, the cross sections of the side insulators 120, 121, and 122 in FIG. 1A may be of any geometry, including circular, elliptical, rectangular, or non symmetric 'D' shaped. The insulator cross sections may match that of the electrodes so that if, for example the electrode cross sections are 'D' shaped and slotted, the insulators 120, 121 and 122 are D-shaped and function to separate the slotted D-tube electrodes 161 from the D-tube electrodes 162. The side insulators 120, 121, and 122 may also be hollow to allow push/pull wires and/or signal wires and conduits or tubes to be inserted through. The side insulators 120, 121, and 122 can be constructed of Polyether Ether Ketone (PEEK) or any other non-conductive insulator material. The melting temperature of side insulators 120, 121, and 122 should be high enough so as not to melt during ablation (e.g., it may be desirable that the melting temperature of the insulator be higher than 400 degrees Fahrenheit).

In the embodiment shown in FIG. 1A, there are corner insulators 121*a-z* that can be rigid D-shaped insulators and function to separate D-tube electrodes 162 from coil electrodes 163. The corner insulators 121*a-z* can be constructed of polyimide or any other non-conductive insulator.

In the embodiment shown in FIG. 1A, there is a distal insulator 122 that can be constructed of a strip of non-conductive material. The distal insulator 122 functions to separate the coil electrodes 163 and to give the electrodes 163 single plane flexibility. The distal insulator 122 can also be highly flexible to fold to allow the two base electrodes 163 to fold up themselves when the head 110 is collapsed and inserted into the sheath 130.

The handheld implement 101 can have various geometric adjustments applied through operating controls on the handpiece 180 of the handheld implement 101. The operating controls may allow for adjusting the electrodes 160*a-z* to fit the perimeter of organs of various sizes and shapes. For a triangular shaped hollow organ cavity such as the human female uterus, the adjustments can be configured to allow independent adjustment of the base and length of the triangle. For an elliptical shape, the adjustments could be major and minor elliptical dimensions. For cavities of other shapes, the appropriate dimensional adjustments can be implemented. The adjustments to fit the cavity dimensions can be used to determine overall therapeutic energy dose in Joules, or other settings such as power, time, etc.

The sheath 130 can be attached to the handpiece 180 and functions to shield the electrodes 160*a-z* while the handheld implement 101 is being inserted into an aperture of a hollow body organ (when the device is collapsed). The sheath 130 can shield at least the side electrodes (161, 162) or all electrodes 160*a-z* during insertion of the device through the organ aperture. The sheath 130 can be constructed to have an atraumatic tip. When collapsed, the head 110 can slide into the sheath 130. Alternatively, the user can slide head 110 out of the sheath 130 as much as desired during a procedure. The sheath 130 can be attached to via a rigid coupling to length adjustment 182 (e.g., knob or attachment), such that moving the length adjustment moves the sheath in the same direction by the same amount as the movement of the length adjustment.

The tube 133 may be a part of aspiration device 103, and may carry fluids from the cavy to reservoir 113. In some embodiments, the tube 133 is attached to a small pump that allows for mechanically pumping the fluid into the tube 133 and collecting the fluid in the reservoir 113. The tube 133 can be constructed of any material that is rigid enough to form a tube and allows for sterilization. In some embodiments, the tube 133 is composed of plastic, rubber, or metal. The tube 133 can be inserted through the handheld implement 101 and sheath 130 to allow insertion through the organ aperture during the procedure. In an embodiment, tube 133 and reservoir 113 form a complete seal such that air cannot enter the reservoir 113 during the process of ablation.

The aspirator port 140 located on the handpiece 180 is connected to an aspirator device 103, via tube 113 (and aspiration device 103 may include a vacuum source used to evacuate the uterus from any body fluids created from the procedure, for example).

Optionally, connector 150 may be located on the handpiece 180 and functions to connect the electrodes 160*a-z* to the power supply 102, which supplies the RF Energy. The connector 150 may comprise at least one wire per electrode 160*a-z*. The wires can connect from the electrodes 160*a-z*, through the sheath 130 to the handpiece 180 and then out the connector 150 to the power supply 102. The connector 150 can be a plug-in having 6 or more tines. However, connector 150 is not necessary The electrodes 160a-z function to apply the RF power to the organ and/or lining of the organ. Each electrode 160a-z has its own lead (wire) that connects the electrode to the power supply 102. In general ablation apparatus 100 contains segmented electrodes 160a-z interspersed with insulators 120, 121, and 122. In some embodiments, the segmented electrodes 160a-z are configured on the head 110 in a shape that mimics the shape of the hollow body organ. In different embodiments, head 110 may have different shapes. The shape of the head 110 can include a generally triangular shaped, circular shaped, oval-shaped, and/or trapezoidal shape. By generally, this means that the shape can be somewhat rounded, meaning that the corners are not pointed, but are rounded. An example of a trapezoidal shape includes, for example, a square edge at the distal end from the handpiece 180 and a triangular edge at the proximal edge to the handpiece 180.

The electrodes 160a-z can be any type of electrodes known in the art, including slotted D-tube electrodes 161, D-tube electrodes 162, coil electrodes 163, braided metal tube electrodes, bead-chain electrodes, point electrodes, and metallic accordion electrodes (examples can be seen in the other embodiments herein).

In some embodiments, ablation apparatus 100 contains from about 3 to about 50 electrodes, including 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, and 49 electrodes 160a-z. In the embodiments, shown in FIG. 1, there are six electrodes 160a-z located on the distal end (e.g., the base) of ablation apparatus 100.

The electrodes 160a-z can be configured along the perimeter of an opening formed by head 110 (e.g., the perimeter of a triangle for a head designed for ablating the uterus). In an alternative embodiment, there may also be electrodes throughout the middle (e.g., on a line bisecting the triangle and/or throughout ablation apparatus 100 on a fan-like arrangement) and/or on the base of ablation apparatus 100 (e.g., base of the triangle). However, by keeping the electrodes only on the perimeter of the opening (so as to be deployed on the perimeter of a body cavity), the diameter head 110 while folded and the diameter of sheath 130 can be kept smaller than when there are electrodes within the opening formed by the head, so that inserting the sheath into the cavity creates less discomfort to the patient and is less invasive. The electrodes 160a-z function to deliver the RF energy to the tissue. By maximizing the circumference and therefore the area of the electrodes, the charge on the electrodes is spread out over a larger area, and therefore less concentrated. The larger surface therefore makes it less likely that the electrodes will char the uterus or another hollow organ during ablation. In the case where the electrode dimensions are round and tubular, only the outermost semicircular surface of each round tubular electrode is in contact with the perimeter of the surface area of the hollow organ, with the innermost semicircular area not contributing to effective contact. In the case of the round a tubular, it is possible to remove the innermost semicircular region to form a tubular electrode with a "D" cross section. The "D" cross section allows for efficient packing of right and left halves of the head 110 (e.g., electrodes 160a-z) when folded up prior to deployment, reducing the overall dimensions of the handheld implement 101 for either insertion through a natural orifice, or through an incision. This can be important when attempting to minimize handheld implement 101 cross-sectional area for minimal trauma to the patient or to reduce anesthesia requirements to control pain. The cross section of two circular electrodes within a tube of radius r can be calculated as follows. Each electrode has a radius or $r/2$, and each has a circumferences of $2(r/2)\pi=r\pi$. The surface area of each these electrodes is $Lr\pi$. If the same tube is filled with two D-shaped electrode, each D-shaped electrode can have a circumference of $2r\pi/2+2r=r\pi+2r=r(\pi+2)$, and the surface area is $Lr(\pi+2)$. The ratio of the largest part of D-shaped electrodes to the largest pair of circular electrodes that fits into the same tube is $2Lr(\pi+2)/(2Lr\pi)=1+2/\pi=1.6366\sim1.64$. Thus, the D-shaped semicircular electrodes have about a 64% larger surface area than the circular electrodes. However, if the corners of the D are rounded, although the D-shaped electrodes will still have a larger surface area, the D-shaped electrodes will not have a 64% larger surface area. Since in particular, it is believed that the pain associated with requiring dilation of an elastic natural orifice, in particular the uterine cervix, is dependent on the diameter of the dilated orifice, the D-shaped electrodes cross-sectional geometry allows for a greater contact area with the hollow body organ tissue without the additional pain associated with the further dilation required by a folded device cross sectional area of two circular tubes. Thus, in some embodiments, the electrodes are D-tube electrodes (161, 162), which make it easier to configure the ablation apparatus 100 to close up into a compact structure and which reduces the density of the energy at the electrodes, thereby allowing the electrodes to deliver a large amount of energy to the uterus for ablation. Using the D-shaped electrode the cross sectional area of the sheath holding the head while the head is folded is minimized or at least reduced to be significantly less than would be required for electrodes having a circular cross section to achieve a similar quality of ablation (e.g., depth of ablation in the center other of the head without charring or otherwise over heating the perimeter). Other noncircular shapes that reduce the necessary diameter of the sheath that holds the head could be used.

The handheld implement 101 can collapse upon itself using any methods known in the art. The embodiment in FIG. 1A, shows a method that involves pulling the side of the electrode portion of the device of head 110 into a sheath 130, which folds insulator 122 and causes electrodes 162 to meet one another and electrodes 163 to meet one another and electrodes 161 to meet each other. In some embodiments, the handheld implement 101 may have push/pull wires attached to the inside of the distal portion of the slotted D-tube electrode 161 on the round side. Pushing on these wires would cause the D-tube electrodes 162 to bend outward, causing the overall width of the handheld implement 101 to increase. In some embodiments, an insulating layer is attached to the flat sides of the slotted D-tube electrodes 161 and/or D-tube electrodes 162 and/or coil electrodes 163 to keep the D-tube electrodes from shorting out when the handheld implement 101 is collapsed and/or from shorting in the region near the opening of the sheath while deployed.

In some embodiments, there are two coil electrodes 163 along the distal edge of the handheld implement 101 (distal from the handpiece 180). The two coil electrodes 163 allow for lateral expansion and retraction. Tubular electrodes along the side 160a-z can alternate with coil electrodes 163.

To increase the penetration of the radio frequency energy without causing charring of the tissue surface near the electrodes, it is also possible to cool the electrodes 160a-z by various means, including running flowing fluid through the ablation apparatus 100 or using gas expansion, phase change, or other means. However, tubes for bringing cooling fluids to the cavity tend to increase the diameter required for the sheath 130.

In the embodiments shown in FIG. 1A, there are two slotted D-tube electrodes 161 proximal to the sheath 130. The slotted D-tube electrode may be a stainless steel D-tube that has cuts in the round side of the "D" which allows the electrode to flex along the flat side of the "D". The slotted D-tube electrodes 161 can be oriented so the flat side of the "D" is pointing towards the middle of the handheld implement 101. In the embodiment shown in FIG. 1A, there are two D-tube electrodes 162 one on each side. The D-tube electrodes 162 are stainless steel D-tubes. The D-tube electrodes 162 can be oriented so the flat side of the "D" is pointing towards the middle of the handheld implement 101. The side D-tube electrodes 162 can be hollow to allow insertion of the electrodes 160a-z and/or insulators 120, 121, and 122 on the base to adjust the width on the base.

In the embodiment shown in FIG. 1A, there are two coil electrodes 163. The coil electrodes 163 can reside inside the D-Tube electrodes 162 and can be slid out via the width adjustment 184 on the handheld implement 101. The coil electrodes 163 can be D-shaped.

The handpiece 180 functions to allow the user to position the handheld implement 101 to change the shape of the handheld implement 101 and/or to collapse the head 110 (e.g., generally triangular electrode end) of the handheld implement 101. The power supply 102 and/or controller 104 can be connected to the electrodes 160a-z via a connector 150 on the handpiece 180. While folding, electrodes 163 slide into an opening at one end of insulators 121, and while unfolding, electrodes 163 slide out of an opening at one end of insulator 121. While folded electrodes 161 may be stored in the hollow space within insulators 120, insulators 121, and/or the electrode 162 between insulators 120 and 121. The hollow space within electrode 162 may be insulated so that head 110 is functional while electrodes 163 are partially within the hollow space within electrodes 162, and head 110 is not fully unfolded. Insulating the interior surface of the electrodes 162 allows electrodes 162 to not short with electrodes 163 when not fully unfolded and allows head 110 to adjust to cavities of different sizes, and still be operational.

The handpiece 180 may include a connector 150, an aspirator port 140, the length adjustment 182 and a width adjustment 184 for deploying the device. The length adjustment 182 is located on the handpiece 180 and can be knobs, sliders, etc. The length adjustment 182 functions to change the effective length of the deployed device to accommodate a variety of different sized organs. The length adjustment 182 changes the length of the sides of the generally triangular head of the head 110 and can pull the sheath back, exposing more and more of the device. The length adjustment 182 allows for pushing the sheath 130 completely or almost completely over head 110 to allow for insertion through a small aperture, such as by the use of pull wires, push wires, and/or a combination thereof.

The width adjustment 184 is located on the handpiece 180 and can be knobs, sliders, etc. The width adjustment 184 functions to change the maximum width of the deployed device to accommodate a variety of different sized organs. The width adjustment changes the size of the base of the generally triangular head of the device 110. In the embodiments shown in FIG. 1A, the width adjustment 184 can push out the coil electrodes 163, allowing the device to open up wider (e.g., the base to widen). The width adjustment and/or length adjustment can be attached to pull wires, push wires, and/or a combination of these that are attached to the head 110 at the sides, front or bottom to effect moving of the sides or base. The push and/or pull wires can be inserted through the side electrodes 160a-z and/or insulators 120, 121, and 122.

Although in the embodiment of FIG. 1A length adjustment 182 and width adjustment 184 are implemented by sliding two knobs within slots that are parallel to one another, in another embodiment (e.g., which will be discussed further below in conjunction with FIG. 7) the knobs may slide is slots that are perpendicular to one another.

Foot control 186 may be used for starting and/or stopping the ablation. By providing foot control 186, both of the user's hands are free for manipulating handheld implement 101 and/or controller system 104.

Figure 1B:
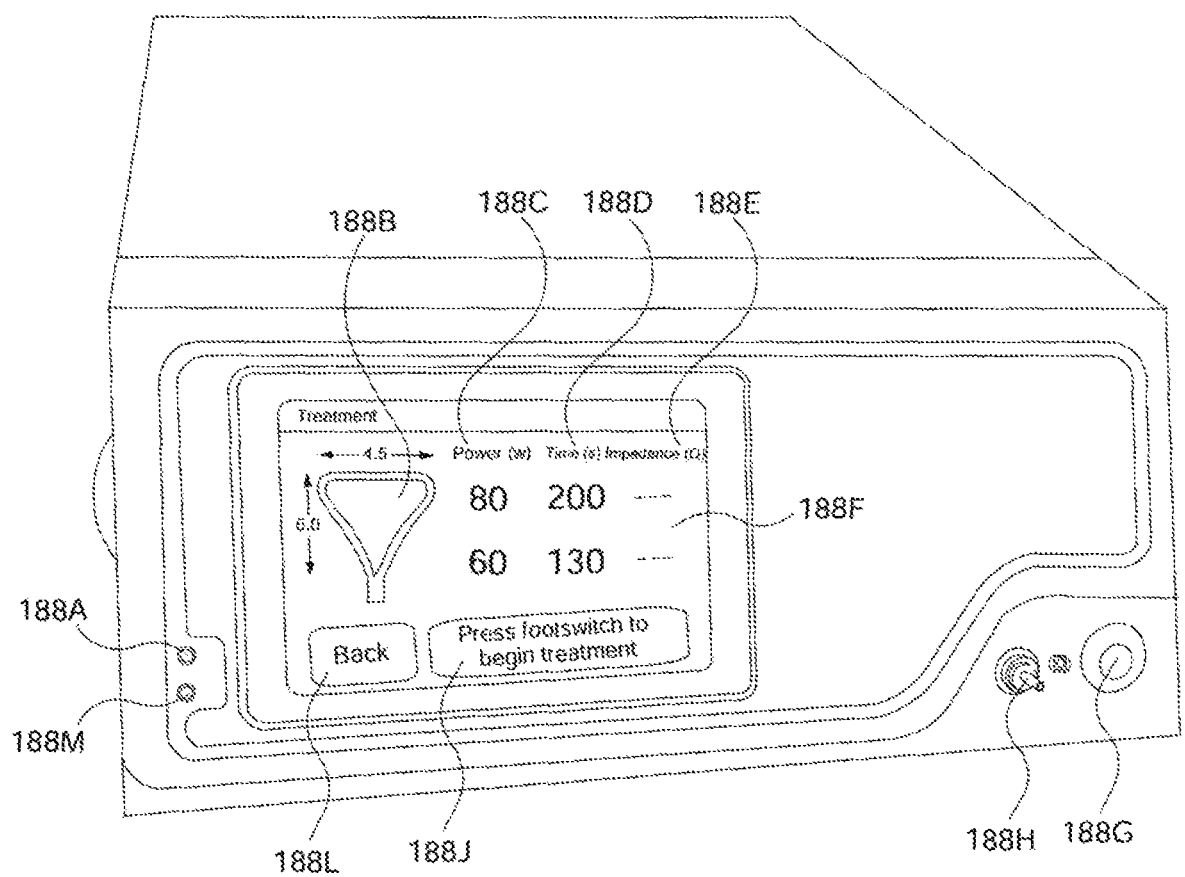
FIG. 1B shows a screen shot of one screen of a user interface of the controller system.

FIG. 1B shows controller system 104 and a page of the user interface associated with controller 104. Controller system 104 of FIG. 1B may include on-light 188a, head image 188b, power column 188c, time column 188d, impedance column 188e, screen 188f, voltage port 188g, aspiration port 188h, instruction box 188j, back button 188l, and warning light 188m. In other embodiments, controller system 104 may have other features in addition to and/or instead of those listed in FIG. 1B.

On-light 188a is a light that may turn on to indicate that controller system 104 is on and/or ablation is currently in progress. Head image 188b is an image of head 110, which indicates the current width and length settings that of controller system 104, which may be used for determining an appropriate power output and duration of ablation for modes 1 and 2. Changing the width and length settings of the head may change the power output and duration of ablation that is determined by controller system 104 to be appropriate. Power column 188c is optional and shows a column of numbers that indicate the power that will be applied during modes 1 and 2 of ablation if the current settings are used (modes 1 and 2 will be described below in conjunction with FIG. 1D). Time column 188d is optional and shows a column showing the duration of time that the power of the corresponding row in the power column may be applied during ablation. In an embodiment, there are two rows. One row (e.g., the top row) contains the power and time associated with mode 1, and the second row (e.g., the bottom row) contains the power and time associated with mode 2. Impedance column 188e is optional, and shows the impedance measured for the region in which the corresponding mode is being applied. In an embodiment, the impedance in the top row is the impedance measured for the region in which mode 1 is being applied, and the impedance in the bottom row is the impedance measured for the region in which mode 2 is being applied. The impedance measurement could be used as an indication as to whether or not controller system 104 is functioning properly. For example, if the impedance is significantly lower or higher than expected for the cavity of interest, it may be an indication that controller 104 is not functioning properly and/or that there is something unexpected present or missing from the cavity of interest. Screen 188f is the screen on controller 104 upon which output information is displayed. Voltage port 188g may be used for connecting handheld implement 101 to controller system 104. The voltage port 188g may deliver the appropriate voltage to the electrodes of head 110 to deliver a desired power for a desired period of time to cause an appropriate ablation of the walls of the cavity of interest. Aspirator port 188h may be used for connecting a tube via which fluids may be evacuated from the cavity of interest. In an embodiment, controller 104 includes a pump that may be used for removing fluids from the cavity of interest. In contrast to other devices, however, it is not necessary to create a vacuum in the cavity of interest to effectively ablate the cavity of interest. Instruction box 188j is optional, and may contain instructions to the user, such as how to start ablation, a parameter was not yet inputted, how to input settings, and/or other messages. Back button 188l may be used to return to a prior screen to enter settings, such as the width and length of the head while in the cavity of interest. Warning light 188m may be used to indicate a problem, such as a short circuit or that a parameter has not yet been entered.

FIG. 1C shows a screen shot of another screen of a user interface of the controller system. FIG. 1C shows on-light 188a, voltage port 188g, aspirator port 188h, instruction box 188j, back button 188l, and warning light 188m, which were discussed above in conjunction with FIG. 1B. FIG. 1C also shows width setting 190B, length setting 190c, screen 190d, decrement button 190h, increment button 190i, and next button 190g. In other embodiments, controller system 104 may have other features in addition to and/or instead of those listed in FIG. 1C.

Width setting 190b may display the width input by the user. Length setting 190c may display the length input by the user. The width and length setting may be entered via a keypad, increment, and/or decrement buttons. Alternatively, the length and width settings may be entered via fields on the display of controller 104 and/or may be determined automatically based on by detecting the positions of the length adjustment 182 and width adjustment 184 (FIG. 1A). Screen 190d may be used for viewing and/or entering the width and length settings of controller 104. Decrement button 190h may be used for decrementing the length and or width setting of controller 104. Increment button 190i may be used for incrementing the length and/or width setting of controller 104. Controller 104 may have a touch screen, keypad, and/or tracking device via which one of the width setting 190b or the length setting may be selected. Upon activation (e.g., by touching the screen or entering input via a tracking device or keypad), decrement button 190h or increment button 190i may be used to decrement or increment, respectively, the current setting that is selected (width or length). Next button 190g may be used to go to the next page of the user interface of controller system 104.

Figure 1D:
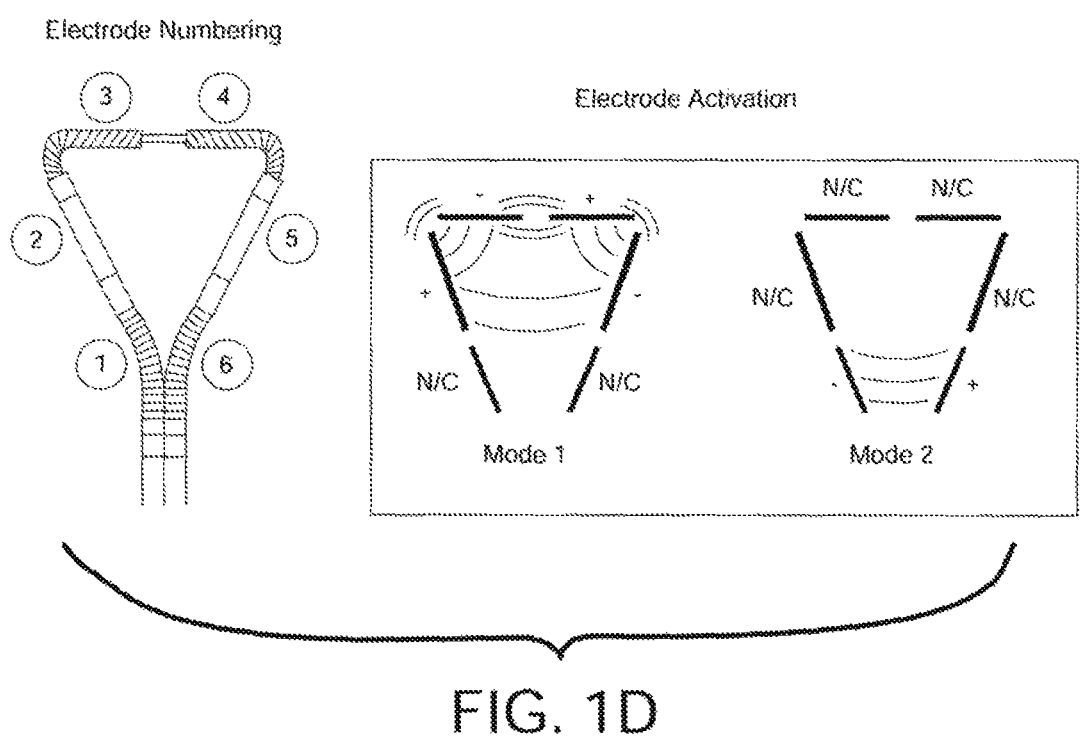
FIG. 1D shows a drawing of an embodiment of electrode activation for an embodiment of a hollow body ablation device having 6 electrodes and two modes.

FIG. 1D provides an example in an embodiment in which ablation apparatus has 6 electrodes. In FIG. 1D, the six electrodes are numbered 1-6. Electrodes 161 may be an embodiment of one of electrodes 1 and 6, electrodes 162 may be an embodiment of one of electrodes 2 and 5, and electrodes 163 may be an embodiment of one electrodes 3 and 4 (FIG. 1A). In mode 1, the top four electrodes are activated such that electrodes 3 and 5 have a negative charge while electrodes 2 and 4 have a positive charge, and electrodes 3 and 5 have a positive charge while electrodes 2 and 4 have a negative charge. As the AC current applied to electrodes 2-5 alternates, which pair of electrodes (the pair having electrodes 3 and 5 or the pair having electrode 2 and 4) is positive and which pair is negative alternates. In mode 2, one of electrodes 1 and 6 is positively charged and the other is negatively charged. An alternating voltage is applied to electrodes 1 and 6, such that which of electrodes 1 and 6 is positively charged and which is negatively charged alternates. In an embodiment, first mode 1 is applied to electrodes 2-5, using a particular voltage and duration of time of application, and then mode 2 is applied using a different voltage and for a different duration of time. The region enclosed within electrodes 2-5 is larger then the region between electrodes 1 and 6, and therefore (e.g., during mode 1) voltage is applied for a longer duration of time and/or the voltage applied is higher, when compared to the voltage applied to electrodes 1 and 6 (e.g., during mode 2). Applying more energy and power to electrodes 2-5 than to electrodes 1 and 6 facilitates ablating the cavity without charring or otherwise over ablating the region between electrodes 1 and 6. In an embodiment, the power applied during modes 1 and 2 and the duration of time that the power is applied during modes 1 and 2 is given in Table 1, below.

TABLE 1

| Parameters for Power (watts) and Time (seconds) | | | | | | |
|---|---|---|---|---|---|---|
| W (cm) × L (cm) | 4.0 | 4.5 | 5.0 | 5.5 | 6.0 | 6.5 |
| Mode 1 Power (W) | | | | | | |
| 2.0 | 58 | 59 | 61 | 63 | 64 | 66 |
| 2.5 | 58 | 59 | 61 | 63 | 65 | 67 |
| 3.0 | 58 | 59 | 61 | 63 | 66 | 69 |
| 3.5 | 60 | 62 | 63 | 66 | 69 | 72 |
| 4.0 | 65 | 67 | 68 | 71 | 74 | 77 |
| 4.5 | 70 | 71 | 73 | 75 | 78 | 82 |
| Mode 2 Power (W) | | | | | | |
| 2.0 | 18 | 23 | 28 | 32 | 37 | 42 |
| 2.5 | 18 | 23 | 28 | 32 | 37 | 42 |
| 3.0 | 18 | 23 | 28 | 32 | 37 | 42 |
| 3.5 | 20 | 24 | 28 | 33 | 37 | 42 |
| 4.0 | 23 | 27 | 30 | 34 | 38 | 42 |
| 4.5 | 26 | 29 | 32 | 35 | 39 | 42 |
| Mode 1 Time (sec) | | | | | | |
| 2.0 | 60 | 60 | 60 | 60 | 60 | 60 |
| 2.5 | 72 | 72 | 72 | 72 | 72 | 72 |
| 3.0 | 84 | 84 | 84 | 84 | 84 | 84 |
| 3.5 | 96 | 96 | 96 | 96 | 96 | 96 |
| 4.0 | 108 | 108 | 108 | 108 | 108 | 108 |
| 4.5 | 120 | 120 | 120 | 120 | 120 | 120 |
| Mode 2 Time (sec) | | | | | | |
| 2.0 | 30 | 30 | 30 | 30 | 30 | 30 |
| 2.5 | 30 | 30 | 30 | 30 | 30 | 30 |
| 3.0 | 30 | 30 | 30 | 30 | 30 | 30 |
| 3.5 | 30 | 30 | 30 | 30 | 30 | 30 |
| 4.0 | 30 | 30 | 30 | 30 | 30 | 30 |
| 4.5 | 30 | 30 | 30 | 30 | 30 | 30 |

In each of the four tables of table 1, the choice of the row is based on the width of the cavity, while the choice of the column is based on the length of the column. The units of widths and lengths are given in centimeters, time is in seconds, and the units of power are in Watts. So, for example, for a uterus that is 3 cm wide and 5.5 cm long, during mode 1, 63 Watts may be applied for 84 seconds, and during mode 2, 32 Watts may be applied for 30 seconds. Table 1 was determined experimentally by placing head 110 a small triangular cavity approximating the uterus between two pieces of meat, then treating meat with head 110, and finally measuring the depth of treating of the meat. The power applied may be determined by iteratively applying a voltage, measuring the current and determining the power for the product of P=IV (power=current times voltage). Depending on whether the power is too high or too low, the voltage is raised or lowered and then the current is measured again and the power is computed again to determine whether the output power is within a desired range. The process of adjusting the voltage, measuring the current and computing the power is repeated until the output power is correct (it may take only a few seconds). Optionally, once the current is measured during the initial iteration, the impedance may be calculated, and the calculated impedance may be used to predict the voltage that will give the desired power output.

The optimum values for ablation in humans may be somewhat different than for the meat, but should be similar. In alternative embodiments, electrodes 1 and 6 may be replaced with multiple pairs of electrodes and electrodes 2-5 may be replaced with multiple pairs of electrodes. In alternative embodiments, the cavity may be divided into more than two regions, and there may be more than two modes applied.

Figure 2:
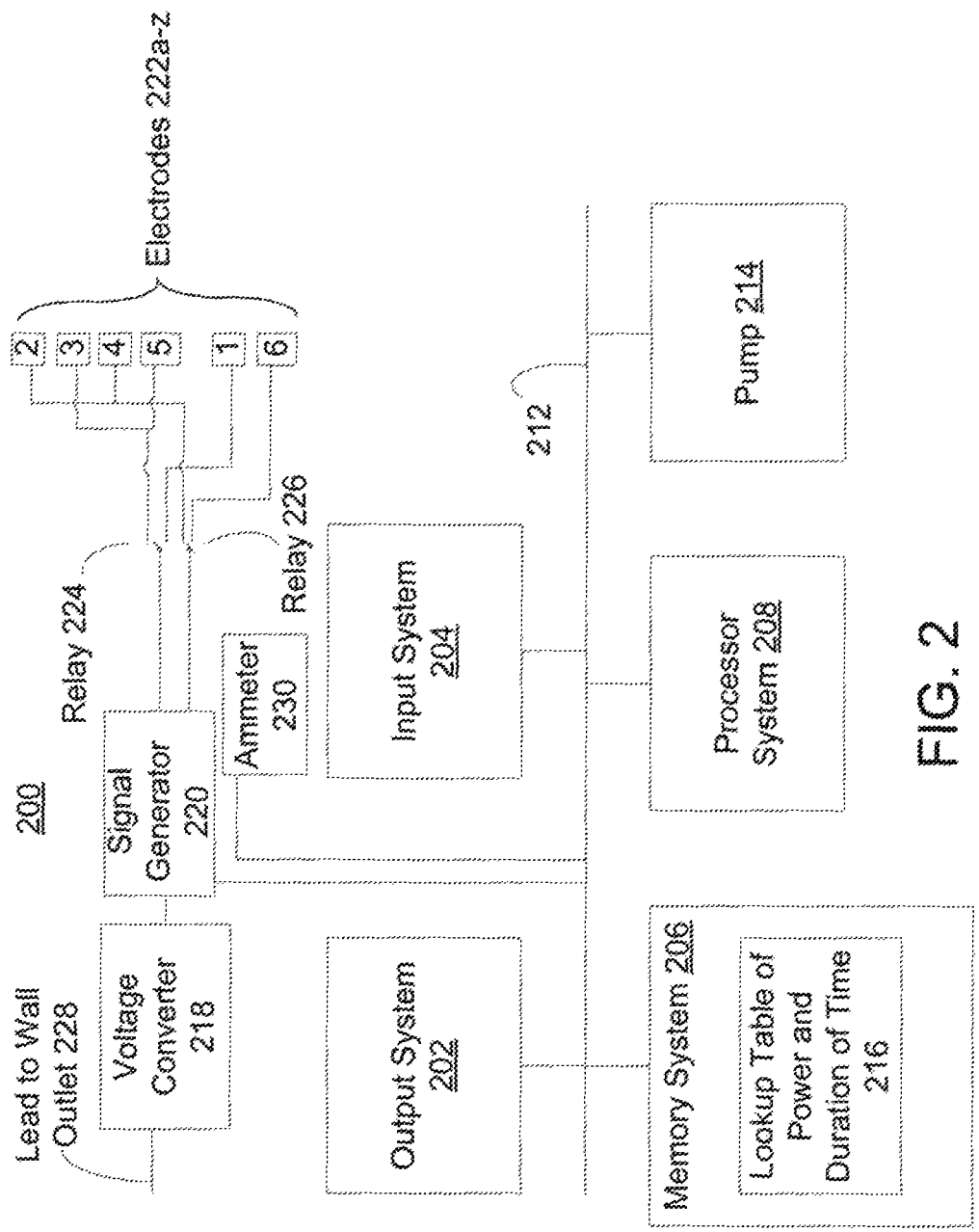
FIG. 2 shows an embodiment of a controller system for a hollow body ablation apparatus.

FIG. 2 shows a block diagram of a controller system 200 used in methods of ablating hollow body organs. The controller may include output system 202, input system 204, memory system 206, processor system 208, communications system 212, vacuum/pressure device 214, algorithm 213, lookup table 216, voltage converter 218, electrode 222a-z, lead 228, signal generator 220, relay 224, relay 226, and ammeter 230. In other embodiments, the controller system used in methods of ablating hollow body organs 200 may include additional components and/or may not include all of the components listed above.

The controller system 200 is an example of a controller that may be used in the ablation apparatus 100 in combination with the power supply 102 to control the radio frequency (RF) amount and treatment length (see FIGS. 1A and 2). Controller system 200 may be an embodiment of controller 104 (FIG. 1A). In some embodiments, the controller controls the frequency of alternating current (AC) from the RF generator to each electrode 160a-z (FIG. 1A) in ablation apparatus 100. Alternatively, the controller 200 can control each set of electrodes 160a-z separately (e.g., the side electrodes and the distal electrodes). With reference to FIG. 1A, the electrodes 160a-z can be separately controlled through separate wires attached from the electrodes 160a-z to the power supply 102 and controller 104. In some embodiments, the controller includes an algorithm that allows for the control of the AC to each electrodes 160a-z. In some embodiments, the controller 200 makes it possible to utilize electrode polarities of various combinations to effect bipolar ablation between selected electrodes. In some embodiments, the controller 200 makes it possible to utilize electrode polarities of various combinations to effect monopolar ablation to a neutral electrode. The RF power source (FIG. 1A, 102) and controller 200 are capable of driving multiple electrodes in various bipolar pairs located along the handheld implement 101 and in proximity to the perimeter of the hollow organ, so as to automatically sequence through the desired set of bipolar or monopolar ablation polarities (e.g., an algorithm).

In some embodiments, the algorithm designed by the controller is an RF power of between about 30 watts and 90 watts, including but not limited to, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, and 89 watts. In some embodiments, the power is applied for a time of between about 10 seconds to about 200 seconds, including but not limited to, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, and 199 seconds. In some embodiments, the method includes more than one mode and/or algorithm. For example, the two modes may be different modes applied to different electrodes at different times. Examples of these modes are discussed above in conjunction with FIG. 1D. In some embodiments, the user can change the amount of time or power during the procedure based on how the mode and/or algorithm is working on the organ they are currently treating and/or based on the dimensions and/or other characteristics of the cavity being ablated. In some embodiments, the power and time parameters are used as shown in Table 1. The width and length are measured and based on the measurements the appropriate parameters used in each mode. In some embodiments, a frequency of between about 360 and 560 KHz is used, including but not limited to 370, 380, 390, 400, 410, 420, 430, 440, 450, 460, 470, 480, 490, 500, 510, 520, 530, 540, and 550 KHz. For example, in an embodiment, the frequency that is used is 460 Hz. In some embodiments, the current is between about 1.4 and 2.4 amps, including but not limited to, 1.5, 1.6, 1.7, 1.8, 1.9, 2.0, 2.1, 2.2, and 2.3 amps. In some embodiments, the current is between 1.5 and 2 amps.

In some embodiments, the voltage is adjusted and the current measured until the power (P=IV) is at the desired value. The current needs to be measured, because the resistance will vary depending on the individual, but for the uterus is of an order of magnitude of about 20 ohms. The width of the uterus is typically between about 2 and 4.5 cm while the length is between about 4 and about 6.5 cm. The endometrium is between about 5 and about 10 mm thick. Under the endometrium is the myometrium. In some embodiments, the ablation does not heat the myometrium.

Output system 202 may include any one of, some of, any combination of, or all of a monitor system, a handheld display system, a printer system, a speaker system, a connection or interface system to a sound system, an interface system to peripheral devices and/or a connection and/or interface system to a controller system, intranet, and/or internet, for example.

Input system 204 may include a key pad and/or touch screen for entering the dimensions of the cavity of interest (e.g., the uterus). Examples of the keypad and touch screen are discussed further in conjunction with FIGS. 1B and 1C. Alternatively, any one of, some of, any combination of, or all of a keyboard system, a mouse system, a track ball system, a track pad system, buttons on a handheld system, a scanner system, a microphone system (e.g., for a voice activated system), a connection to a sound system, and/or a connection and/or interface system to a controller system, connection to a an external storage device such as an EEPROM, S. Dak., MMC, mini-disk or other storage media or medium located in the handpiece, intranet, and/or internet (e.g., IrDA, USB), for example. Input system 204 allows the user to interact with the controller and RF generator to choose an algorithm, power, and/or time for ablation (e.g., by entering the parameters of the cavity). Alternatively, the user may change or vary an algorithm, power and/or time.

Memory system 206 may include, for example, any one of, some of, any combination of, or all of a long term storage system, such as a hard drive; a short term storage system, such as random access memory; a removable storage system, such as a floppy drive or a removable drive; and/or flash memory. Memory system 206 may include one or more machine-readable mediums that may store a variety of different types of information. The term machine-readable medium is used to refer to any medium capable carrying information that is readable by a machine. One example of a machine-readable medium is a controller-readable medium. Memory system 206 may contain one or more saved algorithms that drive multiple electrodes in various bipolar pairs located along handheld implement 101 and in proximity to the perimeter of the hollow organ, so as to automatically sequence through a desired set of voltages applied to different electrodes of ablation apparatus 100. Memory 206 may store lookup tables, such as Table 1, for the determining the pattern, magnitude, and duration of time of the power applied to the cavity (by applying a voltage to electrodes of ablation apparatus 100). Examples of the algorithm and lookup table are discussed above in conjunction with FIG. 1D.

Processor system 208 may include any one of, some of, any combination of, or all of multiple parallel processors, a single processor, a system of processors having one or more central processors and/or one or more specialized processors dedicated to specific tasks. Processor system 208 may implement the algorithms based on the lookup table of Table 1 that are stored in memory 206 and input received from input system 204.

Communications system 212 communicatively links output system 202, input system 204, memory system 206, processor system 208, vacuum/pressure device 214, and/or signal generator 220 to each other. Communications system 212 may include any one of, some of, any combination of, or all of electrical cables, fiber optic cables, and/or means of sending signals through air or water (e.g. wireless communications), or the like. Some examples of means of sending signals through air and/or water include systems for transmitting electromagnetic waves such as infrared and/or radio waves and/or systems for sending sound waves.

Vacuum/pressure device 214 may be included within, attached to, or be an aspirator device (such as aspirator device 103, FIG. 1A). Vacuum/pressure device 214 may include a pump and may be controlled by processor system 208 and/or the keypad of input system 204 may link directly to vacuum/pressure device 214 for turning vacuum/pressure device 214 on and off.

Lookup Table 216 may include values for the settings of the amount of power and time to be used for a hollow body organ of a certain size, stored in memory system 206. Optionally lookup table 216 may include information about the pattern and/or modes in which the voltages are applied. Lookup Table 216 can allow for looking up the size of a hollow body organ by width and length. Table 1 may be an embodiment of lookup table 216. Alternatively, the Lookup Table, or parts thereof may be located in the Handpiece information storage means. In an embodiment, the catheter may include a chip that could configure the generator power delivery scheme by configuring controller 104 or by controller 104 reading the power settings from the chip on the catheter. Having the lookup table on the catheter or on handheld implement 101 allows more flexible energy delivery schemes since it's generally easier to update a disposable portion of hand unit 101 rather than updating controller 104. For example an EEPROM may store lookup table 216, and the EEPROM may be placed in the connector or the housing of handheld implement 101. The EEPROM only requires 3 wires, and three pins of the connector may be used for the EEPROM.

Voltage converter 218 can convert the voltage from the electrical outlet into the voltage needed for ablation of a hollow body organ of a certain size. Voltage converter 218 may include a transformer and/or power supply.

Signal generator 220 may produce a signal of a particular frequency that works with the algorithm needed for ablation of a hollow body organ. For example, signal generator 220 may decide on the frequency and the magnitude of the voltage based on input from processor system 208, that is sent to each electrode for an amount of time (the modes are discussed in conjunction with FIG. 1D, and the electrodes are discussed below in conjunction with electrodes 222a-z).

The electrodes 222a-z can function to transfer the signal to the part of the hollow body organ electrodes 222a-z are in proximity to. Electrodes 1-6 of FIG. 1D, 161, 162, 163, and/or 160a-z, may be embodiments of Electrodes 222a-z. In some embodiments, the electrodes can function in pairs, triplets, quadruplets, quintuplets, or may all function together. In some embodiments, electrodes most distal to handpiece 180 function for a different time and for a different power than the electrodes proximal to handpiece 180 (FIG. 1A).

Relays 224 and 226 may function to relay the signal from the signal generator to one or more groups of electrodes that are included within electrodes 222a-z. A relay (e.g., 224 and/or 226) is an electrically operated switch. In an embodiment, relays 224 and/or 226 use an electromagnet to operate a switching mechanism mechanically, but other operating principles are also used. Relays 224 and 226 allow the signals from signal generator 220 to switch which group of electrodes signals are sent. For example, one relay (e.g., 224) may function to send signals to the two electrodes proximal to the handpiece, such as electrodes 1 and 6 during mode 2. The other relay (e.g., 226) may function to send signals to the four electrodes distal from the handpiece, such as electrodes 2-5, during mode 1. Relays 224 and 226 may be replaced with other types of electrical and/or electromechanical switches, such as transistors, threshold diodes, and/or other threshold devices. FIG. 2 provides an example of how the relays can function to send signals separately to different groups of electrodes.

Alternatives and Extensions

Figure 4:
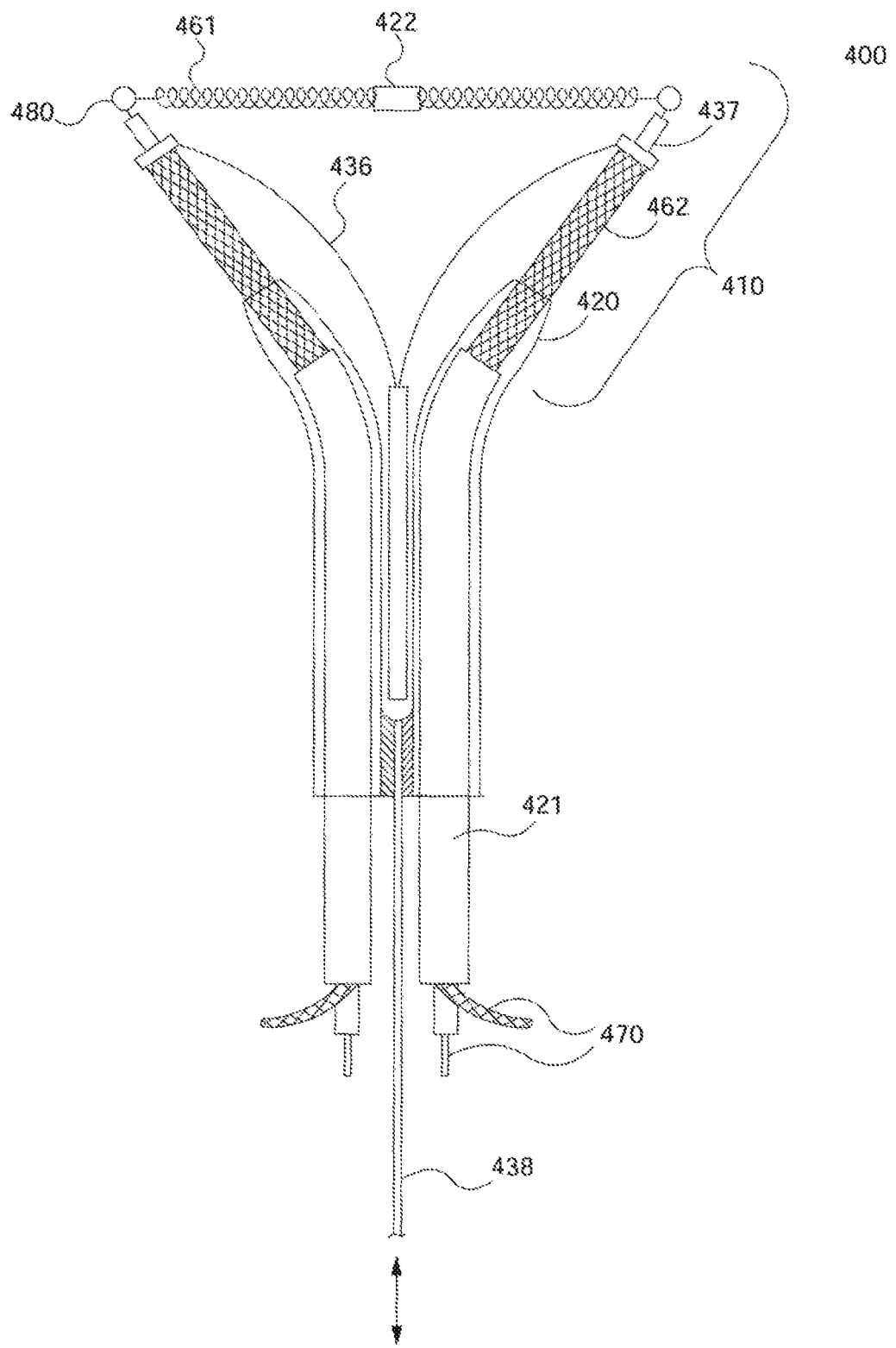
FIG. 4 shows a front elevation view of an embodiment of a hollow body ablation device using extension spring or coil electrodes and push wires.
Figure 5:
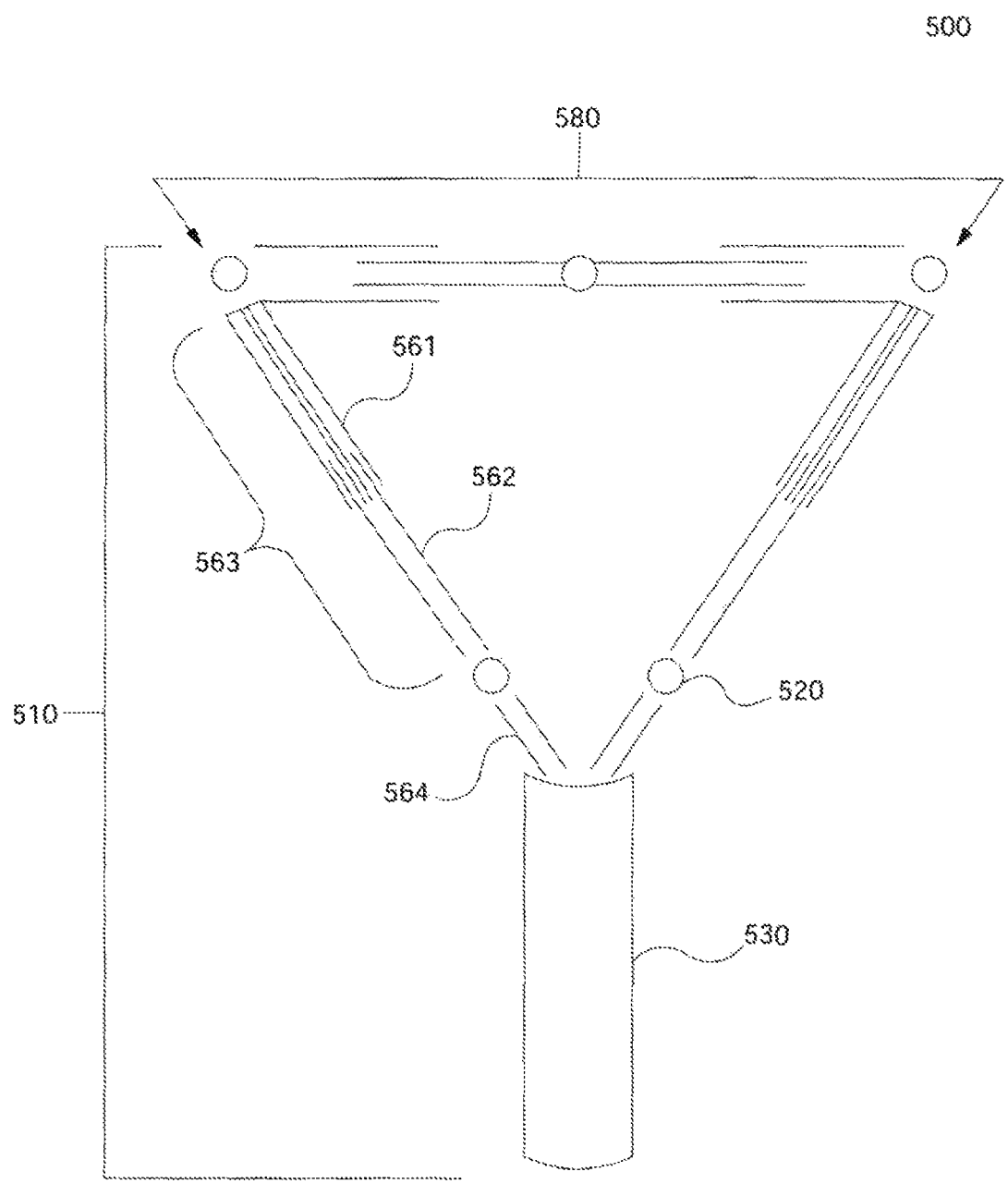
FIG. 5 shows a front elevation view of an embodiment of a hollow body ablation device using telescoping electrodes.

FIGS. 3-5 provide alternative embodiments of the hollow body handheld implement 101 of FIG. 1. In these embodiments, the design, organization, and number of the electrodes can vary. The design and movement of ablation apparatus 100 can also vary. Features of different embodiments can be interchanged with features of other embodiments.

Ammeter 230 measures the current, which is read by processor system 208. Processor system 208 computes the power output based on the voltage setting and the reading from ammeter 230, and adjusts the voltage until the power output is at the desired level as determined by lookup table 216.

FIGS. 3A-C show overhead views of three embodiments of ablation apparatus 100 used in hollow body ablation apparatuses for methods of ablation of hollow body organs. The figures show embodiments of the ablation apparatus 100 show the head without showing the handpiece associated with the head. In some embodiments, the handpiece could be constructed similarly to how handpiece 180 was described in FIG. 1A.

FIG. 3A shows a head 300A having three separate electrodes 304, the center electrode 304 including a sliding insulation sheath 306. The electrodes 304 also include atraumatic tips 302. Although not shown, the head 300A can also include a handpiece 309. In other embodiments the head 300A may not have all of the elements or features listed and/or may have other elements or features instead of or in addition to those listed.

In FIG. 3A, there are three electrodes 304 that can open up in the cavity of the hollow body organ. The three electrodes 304 can open up similar to a fan. Push or pull wires can be used to pull the outer electrodes toward the central electrode 304. The center electrode 304 includes a sliding insulation sheath 306 which can be pushed up when the head 300A is being collapsed. Alternatively, each of the outer two electrodes 304 can be a D-tube electrode having an insulated layer on the straight edge of the D-tube. The straight edge of the D-tube can be placed closest to the middle one of electrodes 304 on each outer electrode 304. In some embodiments, the sheath 306 can be moved up or down on the central electrode 304 using one or more control knobs on the handpiece 309.

The atraumatic tips 302 on the distal ends of the electrodes from the handpiece function to keep the electrodes 304 from touching the sides of the hollow body cavity aperture. Each electrode 304 can have an atraumatic tip 302 on the end of the electrode 304. In some embodiments, the center electrode 304 can be completely covered by the sheath 306 making it unnecessary for it to have an atraumatic tip 302.

The sheath 306 can act as a sliding insulator to keep the outer electrodes 304 from touching the inner electrode 304. The sheath 306 can be a layer of insulation on the central electrode 304 that can slide down the electrode 304, controlling the flow of energy in the hollow body cavity.

Before treatment, the sheath 306 can be positioned to completely or mostly cover the central electrode 304. Positioning sheath 306 to cover central electrode 306 causes the energy to transfer only at the distal portion of handheld implement 101. After that section of the hollow body organ is fully treated, the sheath 306 can be pulled back, exposing more of the electrode 304 and allowing the newly exposed electrode 304 to treat the tissue. Alternatively, the sheath 306 can be positioned to cover the center electrode 304 while handheld implement 101 is collapsed and inserted through the aperture of the hollow body organ and then the head 300A can be opened (e.g., the electrodes 304 separated) and the sheath 306 removed before the RF energy is applied.

FIG. 3B shows an embodiment of an ablation device 300B that uses sliding bead-chain electrodes 312. Using sliding bead-chain electrodes 312 is an alternate approach, for example, for an endometrial ablation device. The ablation device 300B includes side electrodes 336 (shown cutaway), insulator 314, insulator 316, bead-chain electrodes 312, a central push/pull-wire 330, and two side push-pull wires 332. The ablation device 300B can also include a handpiece 309. In other embodiments, ablation apparatus 300B may not have all of the elements or features listed and/or may have other elements or features instead of or in addition to those listed.

The side electrodes 336 can be tubular and hollow in structure and can function to house the bead-chain electrodes 312. The bead-chain electrodes 312 can be a series of metallic beads separated by a thin wire, making the structure very flexible but with a fairly high surface area. The structure of the bead-chain electrodes 312 is similar to what is found on some necklaces and key chains.

The insulators 316 can reside inside the side electrodes 336 and function to insulate the side electrodes 336 from the bead-chain electrodes 312. The insulators 316 can also be attached at the distal end of the device between the two bead chain electrodes 312.

The push/pull wires 334 and 328 can be connected to the bead-chain electrodes 312 and allow the user to extend or retract the bead-chain electrodes 312 as needed. The push/pull wires 334 can pull the sides together to collapse the top two electrodes 312 upon each other creating two straight parallel lines of electrodes 312. A central push/pull wire 332 can be implemented to widen the device 300B. In an embodiment, two sided push/pull wires 332 are made from a flexible resilient material that acts as a spring pushing the head open.

FIG. 3C shows an embodiment of an ablation head 300C that uses metallic accordion electrodes 320. Ablation head 300C is an alternate approach for an ablation device (e.g., an endometrial ablation device). Ablation head 300C can operate very similarly to the sliding bead-chain concept (see FIG. 3B) with the major exception being that, instead of a bead-chain for an electrode, this concept uses a metallic accordion-like structure as the electrode. The accordion structure 320 can be flexible and conductive and can bend as well as change length. Push/pull wires 326 can be used to push the accordion-like electrodes 360 together at the base and/or to push them apart.

FIG. 4 shows an overhead view of an embodiment of an ablation device 400 used in a hollow body ablation apparatus for methods of ablation of hollow body organs. The ablation device 400 uses a central sliding insulator 421 to insulate electrodes 462. The ablation device 400 can use extension spring electrodes 461 for width adjustment and outer push-wires 436 to extend the head 410 from a central push/pull wire 438 attached to a hypotube. The extension spring electrodes 461 and the outer push wires 436 allow for collapsing the head 410 of the device 400 and to change the shape or size of the head 410 of the device.

The ablation device 400 may include a handpiece (not shown), electrodes 460a-z, extension spring electrodes 461, braided metallic electrodes 462, insulators 420, fixed insulators 421, two outer push wires 436, braided tube rings 437, tip connections 480, electrical connections 470, and central push/-pull wires 438, distal insulating gaps 422, sliding insulators 420, and fixed insulators 421. In other embodiments the hollow body ablation apparatus 400 may not have all of the elements or features listed and/or may have other elements or features instead of or in addition to those listed.

The purpose of the sliding insulator 420 is to direct the flow of energy in the hollow body organ. When the sliding insulator 420 exposes only the distal portion of the braided metal tube electrode 462, energy is only delivered to the distal portion of the organ. When the sliding insulator 420 is pulled back, energy is delivered the newly exposed regions until the full uterus is treated.

In FIG. 4, the braided metal tube electrodes 462 are similar to (or may be) coaxial cables and are positioned on the device 400 as side electrodes. Each braided metal tube electrode 462 can have a non-conductive core, in between the outside wires and the inside wires, that would allow braided metal tube electrode 462 to be flexible. The braided metal tube electrodes 462 can be flexible. The braided metal tube electrodes 462 may also contain a ring 437 to keep the braided tubing from unraveling. The braided metal tube electrodes 462 can be attached to the extension springs 461 via connections 480. The connections 480 can be insulators 420 or can be atraumatic materials.

The distal electrodes 461 are extension spring electrodes that may be located at the distal end of the head (on the base of the device 400). The distal electrodes 461 function to treat the distal region of the hollow body organ (e.g., the fundus region of the uterus). The distal electrodes 461 can stretch to accommodate a variety of widths (e.g., uteri widths). The distal electrodes 461 can include a connection 480 that functions to connect the distal electrodes 461 to the center conductive core of the braided metal tube electrodes 462 (e.g., coaxial cable).

The distal insulating gap 422 functions to insulate the extension spring electrodes 461 from each other. The distal insulating gap 422 becomes the tip of the device 400 upon collapsing. The distal insulating gap 422 can be silicone.

The outer push wires 436 allow for width adjustment by connecting to the distal corners of the device 400. The outer push wires 436 push on distal corners and widen the distal end of the device (the base). The outer push wires 436 can extend the extension springs to increase width of the distal end of the head 410. Activation of outer push wires 436 can be at the proximal end of the device (e.g., the handpiece 180).

The sliding insulator 420 functions to collapse the device 400 and/or to widen the device. The sliding insulator 420 slides on top of the braided metal tube electrodes 462 and directs the flow of energy in the hollow body organ (e.g., uterus). The sliding insulator 420 can be moved by connecting a central push/pull wire 438 to it which can be actuated at the proximal end of the device 400 (at the handpiece 180).

The handpiece 180 can be constructed similarly to any embodiment described herein, for example see FIG. 7 and/or FIG. 1A. The handpiece 180 can contain knobs to allow for sliding of the sliding insulator 420 to cover the braided metallic electrodes 462 and/or to collapse the device 400 for insertion into an aperture of a hollow body organ. The handpiece may also contain electrical connections 170 that connect the electrodes 462, 461 to the RF power source.

FIG. 5 shows an overhead view of an embodiment of an ablation device 500 used in a hollow body ablation apparatus for methods of ablation of hollow body organs. The ablation device 500 uses telescoping electrodes 563 to change the length and/or width and/or to collapse the device 500.

The ablation device 500 may include telescoping electrodes 563*a-z*, a sheath 530, joints or electrically insulating couplings 580, a head 510, and a tubular electrode 564. In other embodiments the hollow body ablation apparatus 500 may not have all of the elements or features listed and/or may have other elements or features instead of or in addition to those listed.

The telescoping electrodes 563 may include two pieces 561 and 562. Piece 1 562 and Piece 2 561 can fit together as two sleeves, one sliding into the other sleeve. The dotted line on Piece 2 in FIG. 5 shows a wire for delivering electricity to the electrodes. Using piece 2 561, the length of the telescoping electrode 563 can be changed by moving Piece 1 562 up or down.

Piece 1 562 can be a straight line with an inner polymer tube and two outer hypo tubes glued to the inner polymer tube. The inner polymer tube can be between about 4.0 to 4.6 cm long, including but not limited to 4.1, 4.2, 4.3, 4.4, and 4.5 cm long. In other embodiments, the inner polymer tube is about 4.3 cm long. The two outer hypo tubes can be of a length equal to the length of the inner polymer tube minus a small notch. The length of the notch can be about 1 mm to 3 mm, including 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, and 2.9 mm. The small notch can be filled with glue. The length of the outer tubes can be from about 1 to about 2 cm and from about 2 to about 3 cm long with glue filling the middle notch. In some embodiments, the inner tube is approximately 4.3 cm, and the outer hypo tubes are 1.5 cm and 2.5 cm with glue filling the middle notch.

Piece 2 561 can be a longer piece that is generally with one inner tube, an outer tube that covers and is parallel to the inner tube. Piece 2 561 can include a central tube washer or disk with a narrow polymer tube glued in. The outer tube can be a larger diameter SS hypotubes, sized to fit over and "telescope" the smaller SS hypotubes (Piece 1) 562. When piece 2 561 is inserted over Piece 1 562, it can form a two-section adjustable length electrode (a telescoping electrode) 563.

The electrodes 563*a-z* can be configured on the head 510 such that the telescoping electrodes 563*a-z* are separated from each other by an electrically insulating coupling 520. Two telescoping electrodes 563 are positioned on the base (distal side) of the head 510 separated by a couplings 520*a-z*. One or two telescoping electrodes can also be placed on either side of the head 510. Alternatively, one telescoping electrode 563 can be placed on each side and one proximal electrode 564 can be placed separated by an electrically insulated coupling 520. The proximal electrode 564 can be 1.5 cm long. The telescoping electrode 563 can vary from about 2.5 cm to about 5 cm (depending on whether Piece 1 562 and Piece 2 561 are pulled apart or pushed together). In some embodiments, the telescoping electrodes on the base can vary from about 2 cm to about 4 cm, depending on whether Piece 1 562 and Piece 2 561 are pulled apart or pushed together.

Two of the adjustable telescoping electrodes 563 can form the sides of a triangular shaped electrode structure 510 (the head). The distal end of the triangle (which is the base of the triangle) can be similarly telescoped to have adjustable width. The sides can also include a tubular electrode 564 separated from the telescoping electrode 563 by an electrically insulted coupling 520. The device 500 can also include a sheath 530 that can be moved up and over the head 510 to collapse the head 510 for insertion into an aperture of a hollow body organ.

Further embodiments of ablation devices can include a collapsible flex circuit with a NiTi strip for support (a stronger wire). The NiTi shape memory alloy strip creates a loop shape to fit a uterus or other hollow body organ. NiTi strips are superelastic fine-grained Nickel-Titanium (NiTi) polycrystalline shape memory alloys.

Further embodiments of ablation devices include, for example, a self-expanding spring device with a 2-4.5 cm width when completely open and 4-6.5 cm length when completely open. The springs can be the electrodes or alternatively, the electrodes can be included as "islands" in the springs (e.g., electrodes can be woven into mesh as islands). Another alternative embodiment of an ablation device includes a metalized foam that acts like an accordion fan.

An Embodiment of the Handheld Implement

Figure 6A:
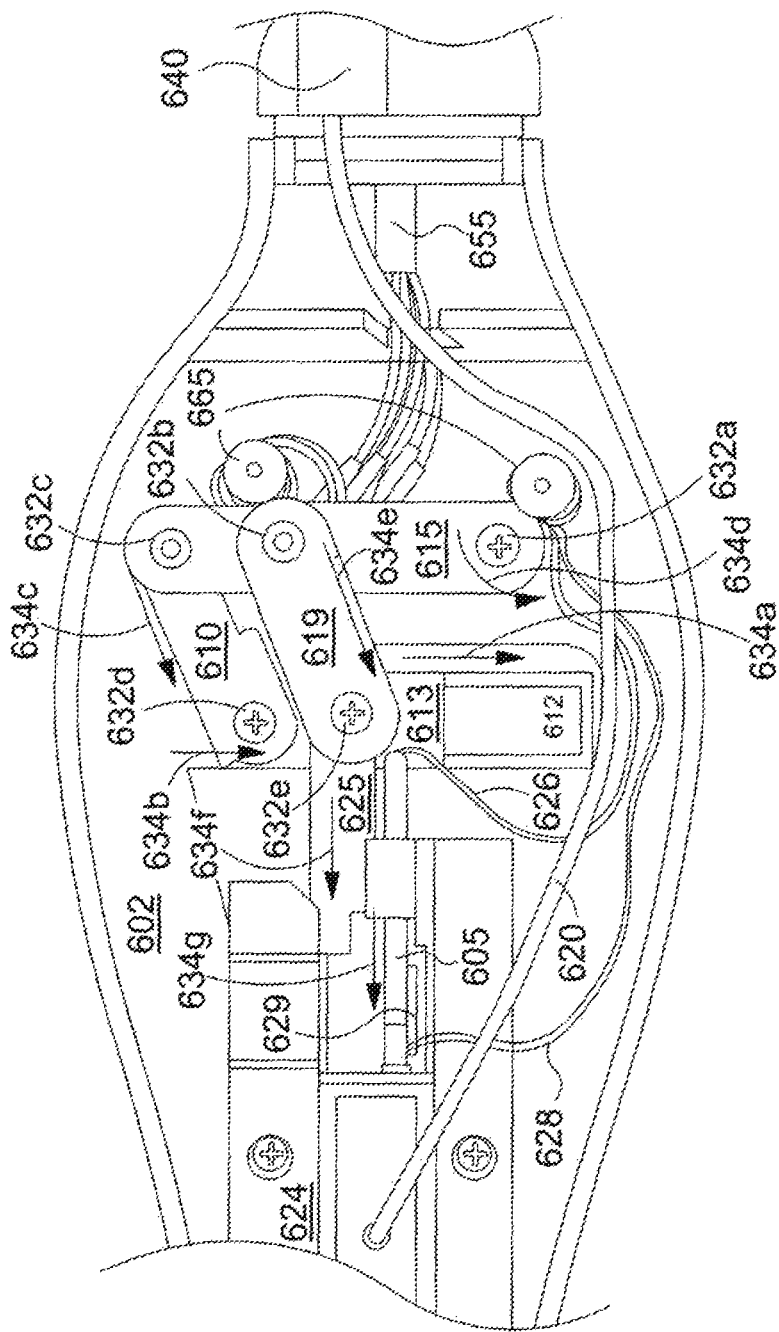
FIG. 6A shows a front elevation view of the inside of an embodiment of the handpiece.

FIG. 6A shows an overhead view of an embodiment of the inside of a handpiece 600 used in an embodiment of a hollow body ablation apparatus for methods of ablation of hollow body organs. The handpiece 600 includes a shell 602, a central tube 605, levers 610, 615, and 619, sliding member 613, width slot 612, aspirator tube 620, chamber 624, sliding piece 625, wires 626, wires 628, length slot 629, joints 632*a-e*, arrows 634*a-g*, a vacuum port 640, a sheath 655, and wire post 665. In other embodiments the handpiece 600 may not have all of the elements or features listed and/or may have other elements or features instead of or in addition to those listed.

In short, the length and width adjustments on the handpiece 600 use push/pull wires attached to levers, sliding members and/or the sheath that function to change the length and width of the ablation device and/or to insert it into the sheath. The push/pull wires are attached to the head of the device and are attached to levers and/or sliding members. Knobs on the handpiece are used to move the levers to effect changes in position and/or to collapse the head into the sheath.

Handpiece 600 is another embodiment that may be substituted for handpiece 180. The outer shell 602 of the handpiece can be in any shape known to the skilled artisan. In some embodiments it is in a shape that makes it more comfortable to the user to hold. In some embodiments, it is small enough that the user can hold it with one hand. The outer shell 602 can be made of a material that is sterilizable without changing its shape and/or properties.

The central tube 605 may be slidably attached to a chamber to which the sheath is connected. The central tube 605 may be attached within the sheath (not shown) to push/pull wires for movement of electrodes 3 and 4 (see FIG. 1D) in and out of the insulating tubes separating electrodes 3 and 4 from electrodes 2 and 5. Central tube 605 may be connected to a sliding piece mounted in channels outside of the walls of the chamber. Central tube 605 may slide inward and outward within a hole in one of the walls of the chamber as the sliding piece slides. Central tube 605 may be referred to as a push/pull tube, and central tube 605 is connected to push/pull wires. Pushing and pulling central tube 605 pushes and pulls, respectively, the push/pull wires pushing conductors 3 and 4 out or pulling conductors 3 and 4 in.

Lever 610, width slot 612, sliding member 613, lever 615, and lever 619 are used for changing the width of the head. The width adjustment can be effected by sliding one of the knobs on the outside of the handpiece 600 right or left on the handpiece within a slot 612. The knob is attached to the sliding member 613, which moves levers 610 and 619. The levers are attached to a push/pull wire. The central push/pull wire 438 has a fork or split where the central push/pull wire 438 divides into two outer push pull wires 436 that are attached to the head/electrodes (3 and 4, FIG. 1D). As the central push/pull wires are 438 is pushed, electrodes 3 and 4 slide out of the insulating D-shaped tubes between conductors 2 and 3 and between conductors 4 and 5 (FIG. 1D). As the D-shaped coil electrodes 3 and 4 extend out of the insulator tubes, electrodes 3 and 4 push against one another (via the insulator separating electrodes 3 and 4), causing the head to widen into a triangular shape. Moving the knob in the opposite direction reverses the process bring electrodes 3 and 4 into the insulating tubes attached to electrodes 2 and 5, respectively. Movement of the knob pulls the distal electrodes (e.g., coil electrodes in FIG. 1A) into insulators and/or the sheath. The movement of the width adjustment can be at a right angle to the movement of the length adjustment so that it will be more clear to the user which knob to use for the width adjustment, which may decrease confusion about which knob causes which adjustment. However, in some embodiments, the width adjustment and length adjustment can move in the same direction (see, for example, the embodiment in FIG. 1A).

The length adjustment includes a length slot 629 a sliding member, and a sheath (not shown). The length adjustment can be effected by sliding a knob up or down a slot 629 on the handpiece 600. The knob may be coupled to the sheath with a rigid coupling, such that moving the knob slides the sheath the same distance and in the same direction as the knob. The slot 629 can be positioned on the handpiece parallel to the sheath and, thus, using the slot on the handheld implement 101, the movement of the knob can mimic the movement of the sheath up or down the handpiece. Thus, the knob is moved upward (distally) to lengthen and down (proximally) to shorten. Further, as the sheath moves up, the head can be collapsed to have the two sides of the base parallel to each other so that the majority of the head fits into the sheath. In this case, the knob is moved to the furthest distal position to collapse the head. Smaller movement of the knob results in smaller changes to the length of the head that is unsheathed.

Chamber 624 may be hermetically sealed. Central tube 605 may slide in an inward and outward direction within a hole in one of the walls of chamber 624, thereby changing the width of head 110, if head 110 is at least partially exposed or unsheathed. The sheath may be slidably attached to chamber 624 and may slide in and out of chamber 624 to expose or cover, respectively, portions of head 110, thereby changing the length of head 110 that is exposed.

Sliding piece 625 may be slidably mounted in channels along side chamber 624. Central tube 605 may be fixedly mounted to sliding piece 625, so that when sliding piece 625 slides, central tube 605 slides with sliding piece 625 in the same direction inward or outward with respect to a hole in a wall of chamber 624.

Wires 626 may attach to electrodes 3 and 4, and wires 628 may attach to electrodes 1, 2, 5, and 6 (see FIG. 1D and FIG. 2). Wires 626 may slide with central tube 605 as the width of head 110 is adjusted.

The wires 626 and 628 function to transmit electricity to the electrodes, which may have a frequency in the radio frequency range, for example. As such, the wires 626 and 628 are attached to the electrodes in the head of ablation apparatus 100, and wires 626 are inserted through the central tube 605 while wires 628 enter chamber 624 on the outer side central tube 605 to attach to electrodes 3 and 4 and electrodes 1, 2, 5 and 6, respectively. Wires 626 and 628 may also be attached through a connector to controller 104. In an embodiment, one set of electrodes (e.g., 1, 3, and 5 of FIG. 1D) is connected to the one polarity of the power source and another set of electrodes (e.g., 2, 4, and 6 of FIG. 1D) is connected to the other polarity of the power source, such that as the polarity of the power source alternates, the polarity of the electrodes alternate. In an alternative embodiment, there is one wire per electrode allowing for separate control of each electrode.

Slot 629 may hold the length adjustment knob, and the length adjustment knob may be rigidly connected to the sheath (e.g., via a plastic connector piece). As the length adjustment knob slides up and down slot 629, the sheath may slide up and down covering or exposing, respectively portions of head 110, thereby adjusting the length of the head 110 that is used for ablation according to the dimensions of the cavity. In some embodiments, as the sheath is moved up and over the head of the device, the width adjustment operates to push the sides together and to push the two sides of the distal end together to create a tubular head that can fit into the sheath (e.g., sheath 130 or 530).

Joints 632*a-e* allow levers 610, 615, and 619 and sliding member 613 to move. In an embodiment, joints 632*a-e* may be pivots, which may be held in place by screws. Joint 632*a* attaches lever 615 to shell 602 so that lever 615 rotates about joint 632*a*. Joint 632*b* attaches lever 615 to lever 619 so that lever 619 may rotate about joint 632b as lever 610 moves (the movement of lever 615 causes lever 619 to move). Joint 632c attaches lever 610 to lever 615 so that lever 610 and 615 rotate with respect to joint 632c as lever 610 moves (which causes lever 615 to move). Joint 632d connects lever 610 and sliding member 613 so that as sliding member 613 slides, lever 610 rotates about joint 632d. Joint 632e connects lever 619 to sliding piece 625, so that as lever 619 moves (and rotates with respect to joint 632e), sliding piece 625 slides pushing central tub 605. Joint 632e is not connected to sliding member 613.

Arrows 634a-g are direction arrows showing the direction of movement of levers 610, 615, and 619, sliding piece 625, and central tube 605 as sliding member 613 slides in the direction of arrow 634a. Specifically, as sliding member 613 slides in the direction of arrow 634a, one end of lever 610 is pulled, via joint 632, in the direction of arrow 634b (which is the same direction as arrow 634a). As a result, the other end of lever 610 is pulled in the direction of arrow 634c. The movement of lever 610, via joint 632c, pulls on one end of lever 615, which causes lever 615 to rotate about joint 632a (which is at the other end of lever 615) in the direction of arrow 634d. The rotation of lever 615 causes lever 615 to push, via joint 632b, on one end of lever 619 in the direct of arrow 634e. The pushing on lever 615 causes the other end of lever 615 to push, via joint 632e, on sliding piece 625. As a result of the pushing on sliding piece 625, sliding piece 625 moves in the direction of arrow 634f, which causes central tube 605 to move in the direction of arrow 634g (which is the same direction as arrow 634f). Moving sliding member 613 (via moving the width adjustment knob) in the opposite direction of arrow 634a causes movement of levers 610, 615, and 619, sliding piece 625, and central tube 605 to move in the opposite direction as arrows 634b-g, in a similar manner as described above (except pushes are replaced with pulls and pulls are replaced with pushes).

The vacuum port 640 allows for the attachment of a vacuum tube to remove fluid (i.e. liquids, vapors and gases) from the hollow body organ before during and after the procedure. The tube can be placed from the vacuum port 640 through the handpiece to effect fluid removal in the hollow body organ.

The sheath 655 functions to connect the wires 626 and 628 to the controller system. In some embodiments, the wires 626 and 628 are bundled into an electrical wire to produce the sheath 655. The sheath 655 may allow for reversible attachment to the controller system to allow for separation of the device from the controller (e.g., via an electrical plug-in).

The wire post 665 functions to immovably attach the wires 626 and 628 from the sheath 655 to insertion through the housing 607.

Figure 6B:
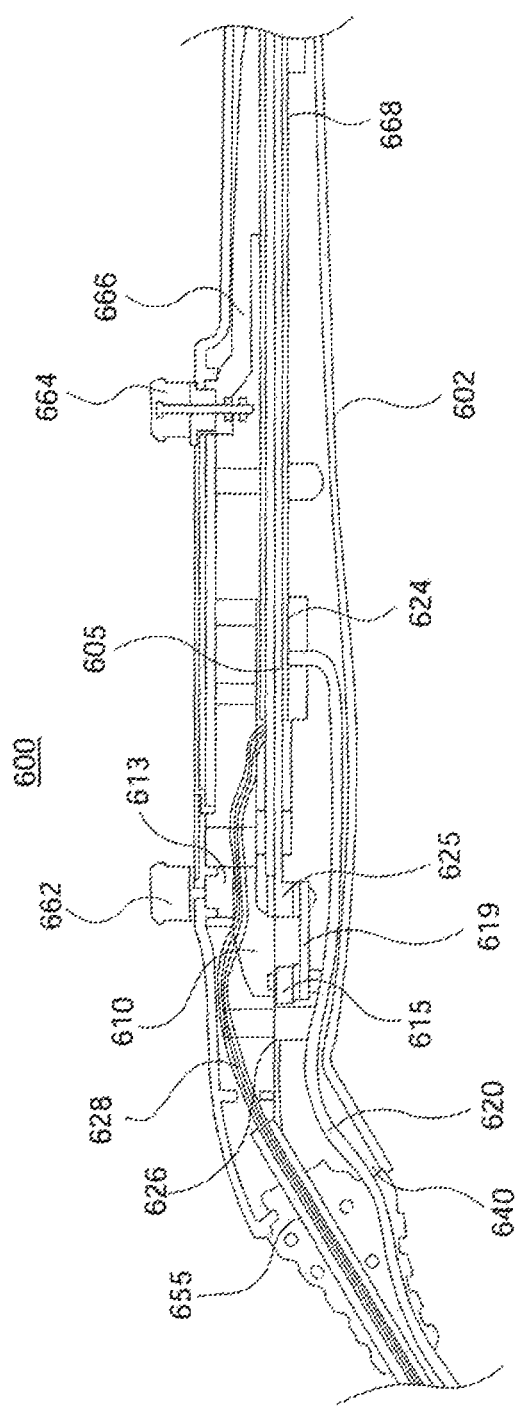
FIG. 6B shows a cross sectional view of an embodiment of the inside of handpiece FIG. 6A.

FIG. 6B shows a cross sectional view of an embodiment of the inside of handpiece 600. The handpiece 600 includes a shell 602, a central tube 605, levers 610, 615, and 619, sliding member 613, an aspirator tube 620, chamber 624, sliding piece 625, wires 626, wires 628, a vacuum port 640, and a sheath 655, and lead-wire post 665, which were discussed above in conjunction of FIG. 6A. Handpiece 600 may also include width knob 662, length knob 664, rigid coupling 666, and sheath 668. In other embodiments the handpiece 600 may not have all of the elements or features listed and/or may have other elements or features instead of or in addition to those listed.

Width knob 662 is rigidly fixed to sliding member 613. Thus when the user slides width knob 662, sliding member 613 slides in the same direction, and levers 610, 615, and 619, sliding member 613 translate the sliding motion of width knob 662 into the sliding motion of central tube 605. Length knob 664 is used for sheathing and unsheathing head 110. Rigid coupling 666 is rigidly attached to length knob 664 and to the sheath so that moving length knob 664 moves rigid coupling 666, which in turn moves the sheath. Sheath 668 is rigidly attached to rigid coupling 666 so that when length knob 662 moves, sheath 668 moves in the same direction sheathing or unsheathing head 110.

Figure 6C:
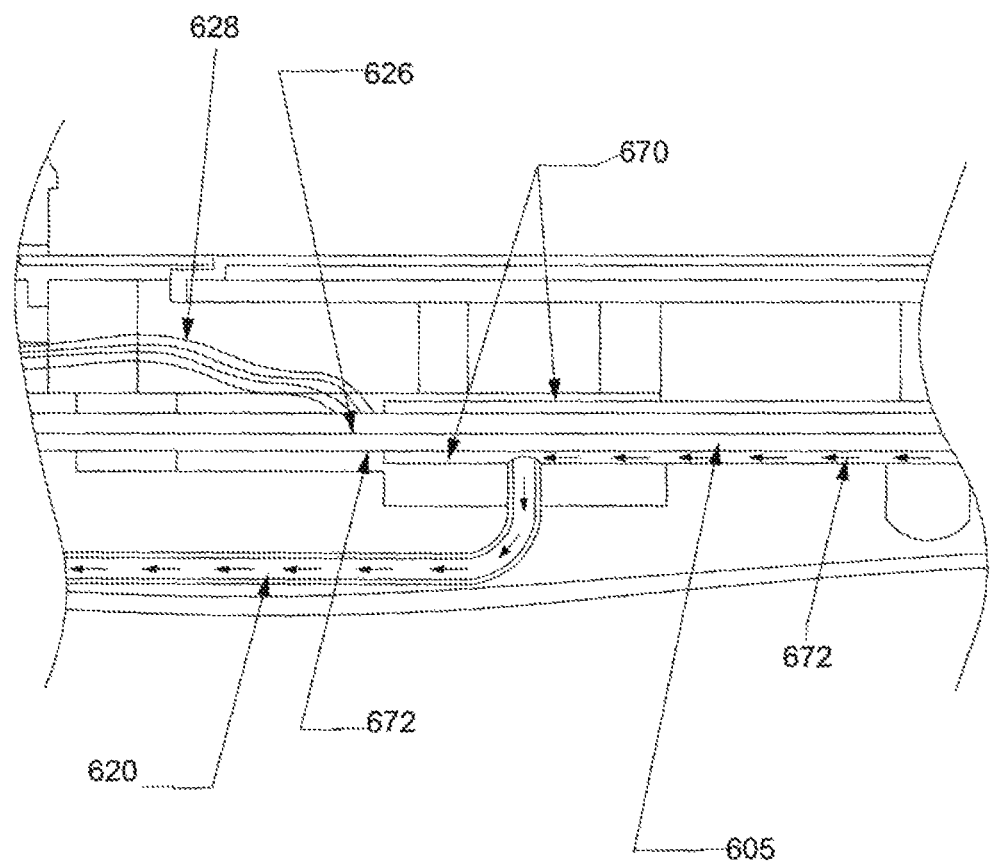
FIG. 6C shows a blowup of a portion of FIG. 6B.

FIG. 6C shows a blowup of a portion of FIG. 6B. FIG. 6C shows central tube 605, aspirator tube 620, wires 626, wires 628, epoxy 670 and close fitting tubing for sealing 672.

FIG. 7 shows an overhead view of an embodiment of the outside of a handpiece 700 used in an embodiment of a hollow body ablation apparatus for methods of ablation of hollow body organs. The handpiece 700 includes an aspirator tube 733, a fluid removal connector 735, an electrical cord 755, an electrical plug in 760, a length adjustment knob 782, a length adjustment groove 783, a width adjustment knob 784, a width adjustment groove 785, width icon 786, length icon 788, width scale 790, and length scale 792. In other embodiments the handpiece 700 may not have all of the elements or features listed and/or may have other elements or features instead of or in addition to those listed.

Handpiece 700 may include a shell constructed of a material that allows for sterilization. The shell functions to enclose the various parts of the hollow body ablation device, including but not limited to, the levers and central push/pull wires necessary to allow change in shape of the device, an aspirator tube, wires for attachment to the electrodes to allow RF energy, and a sheath to allow for covering the head of the ablation device during insertion into the hollow body organ. Shell 602 (FIG. 6A) may be sued as the shell of handpiece 700.

Handpiece 700 may be connected to a controller system (similar to controller system 104), which may include an algorithm that allows for the control of the alternating current (AC) and can be capable of applying different patterns of alternating the polarities of the different electrodes of an ablation apparatus. The frequency, voltage, and/or current may be adjusted to fit the cavity dimensions, and can be used to determine overall therapeutic energy doses, and/or determine other settings such as power, duration (the amount of time) of application of the electric field, etc. The controller is discussed in more detail in conjunction with reference to FIG. 2.

The aspirator tube 733 functions to remove fluid and/or gases from the hollow body organ before, during and after the ablation procedures. The aspirator tube 733 can be inserted through the shell 702 of the handpiece 700 and can be snaked up through an attachment tube 710.

The fluid removal connector 735, functions to attach the aspirator tube 733 to the reservoir and/or pump.

The electrical cord 755, allows for attachment to the controller system 704. The electrical cord 755 and is attached via wires to each electrode on the head of the hollow body ablation device. The wires can be inserted through the connector tube 710 to the electrodes. The wires can be connected via the electrical cord to the controller 704.

The electrical plug in 760, allows attachment of the wires within the electrical cord 755 to the controller system 704. The wires can each be separately controlled by allowing for separate pins within the plug. Thus, in some embodiments there are the same number of pins in the plug as there are electrodes.

The length adjustment knob 782 may be an embodiment of length knob 664, is attached to the sheath and functions to move the sheath up and over the head and/or to pull the two sides of the head together to form a tube for insertion through an opening into a hollow body organ. The length adjustment knob 782 can be rotated to lock the knob in place.

The length adjustment groove 783, allows slideable movement of the knob 782 to choose the amount of lengthening or shortening. When the length adjustment is at the proximal end, the head is completely collapsed and the sheath partially or completely covers the head of the device.

The width adjustment knob 784 may be an embodiment of width knob 662, and is attached to levers within the handpiece that effect movement of central push/pull wires attached to the head to pull each side of the head into or out of the sheath. Alternatively, the width adjustment knob 748 can move the distal electrodes into or out of an insulated tube next to the electrodes on the side of the head. The width adjustment knob 784 can be rotated to lock the knob in place.

The width adjustment groove 785 may be an embodiment of slot 612 and may allow slideable movement of the adjustment knob right and left to increase or decrease the width, particularly the width of the distal end of the head.

As shown in FIG. 7, information can be provided on the outside of the handpiece to help the user use the device. The user can be provided with values to show the amount of widening or lengthening of the head. Other information can include symbols (e.g., + or −) indicating widening or shortening. Further symbols such as carrots can be used to indicate widening and/or shortening. Arrows can be included to indicate the direction of movement of knobs and/or sliding.

Specifically, in an embodiment, width icon 786 indicates to the user that width knob 784 adjusts the width of the head. In an embodiment length icon includes an image of the head with arrows indicating the direction of expansion and contraction, which is along the width of the head at the top of the head. In other embodiments, another icon may be used. Length icon 788 indicates to the user that length knob 782 adjusts the length of the head. In an embodiment the length icon includes an image of the head with arrows indicating the direction of expansion and contraction, which is along the length of the head at the side of the head. In other embodiments, another icon may be used. Width scale 790 indicates the width of the head. Once the user places the head into the cavity and adjusts the head an appropriate amount by sliding width knob 784 the position of the knob on width scale 790 indicates how wide the head has been opened. The reading on width scale 790 of where width knob 786 is located may be entered into the controller, for determining the voltage setting for the ablation. Length scale 792 indicates the length of the head. Once the user places the head into the cavity and adjusts the head an appropriate amount by sliding length knob 782, the position of the length knob 782 on length scale 792 indicates how long the head has been opened. The reading on length scale 792 of where length knob 784 is located may be entered into the controller, for determining the voltage setting for the ablation. Once the width and length settings are entered based on the locations of length knob 782 and width knob 784, the controller automatically determines an appropriate power output for modes 1 and 2 at with to ablate the cavity of interest.

Figure 8A:
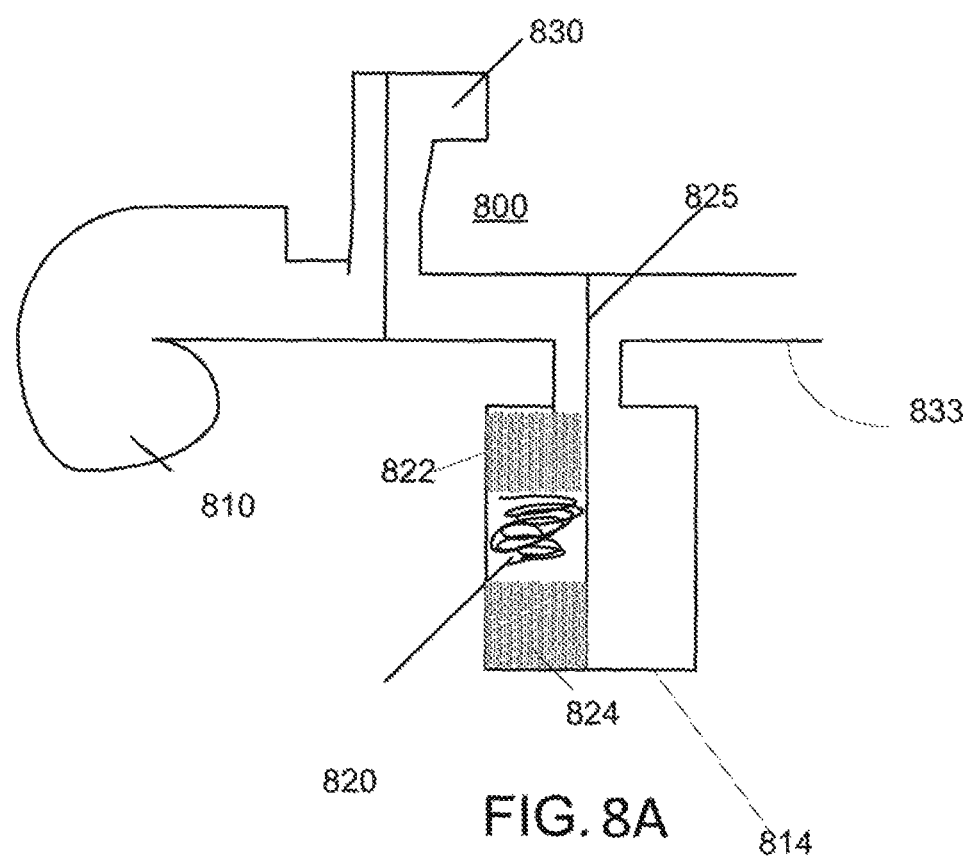
FIG. 8A shows an embodiment of a fluid removal device.

FIG. 8A shows a drawing of an embodiment of the fluid removal system 800 used in an embodiment of a hollow body ablation apparatus for methods of ablation of hollow body organs. The fluid removal system 800 includes a pump 810, a reservoir 814, an activated carbon filter 820, filter media 822, filter media 824, a secondary filter 830, and aspirator tube 833. In other embodiments the fluid removal apparatus 800 may not have all of the elements or features listed and/or may have other elements or features instead of or in addition to those listed.

The pump 810 can be any appropriate pump known in the art that is capable of pulling fluid and/or gases from the hollow body organ and into a reservoir during a procedure. The pump 810 can be attached to a reservoir and separated from the reservoir by filters to ensure that none of the fluid and/or gases end up in the pump and/or that non-sterile air does not come in contact with the hollow body organ. In some embodiments the pump and/or reservoir includes a sterile seal.

The reservoir 814 can be any type of reservoir 814 that can be attached to a pump 810 to allow removal of fluids and/or gases from a hollow body organ into a holding area. In some embodiments, the reservoir is composed of a material that allows for sterilization. In some embodiments, the reservoir includes an activated carbon filter 820 and/or fluid separator 823. In an embodiment, a first layer of filter media 822 is followed by the layer of activated carbon 820, followed by a second layer of filter media 824.

The reservoir 814 can include an activated carbon filter 820 that functions to remove particulates before they come in contact with the pump. "Activated Carbon", also called activated charcoal or activated coal is a form of carbon that has been processed to make it extremely porous and thus to have a very large surface area available for adsorption. The activated carbon filter can be separated from the reservoir by a fluid separator. The reservoir 814 can also include one or more layers of filter media meant to trap large molecules of fluid or vapor, prior to adsorption by the activated carbon material.

The fluid separator 823 can be any type of porous membrane, sieve or screen that allows for the passage of air or gases but does not allow for the passage of fluid or vapor.

The secondary filter 830 can be any type of filter that allows for the passage of air or gases but does not allow for the passage of fluid, vapor or small particles into the pump. The aspirator tube 833 can allow for the passage of fluids and/or gases through a tube to a reservoir. The aspirator tube 833 can be attached to a hollow body ablation device and can be inserted into a hollow body organ during an ablation procedure. The aspirator tube 833 can act to remove fluid and/or gases from the organ during the procedure.

Figure 8B:
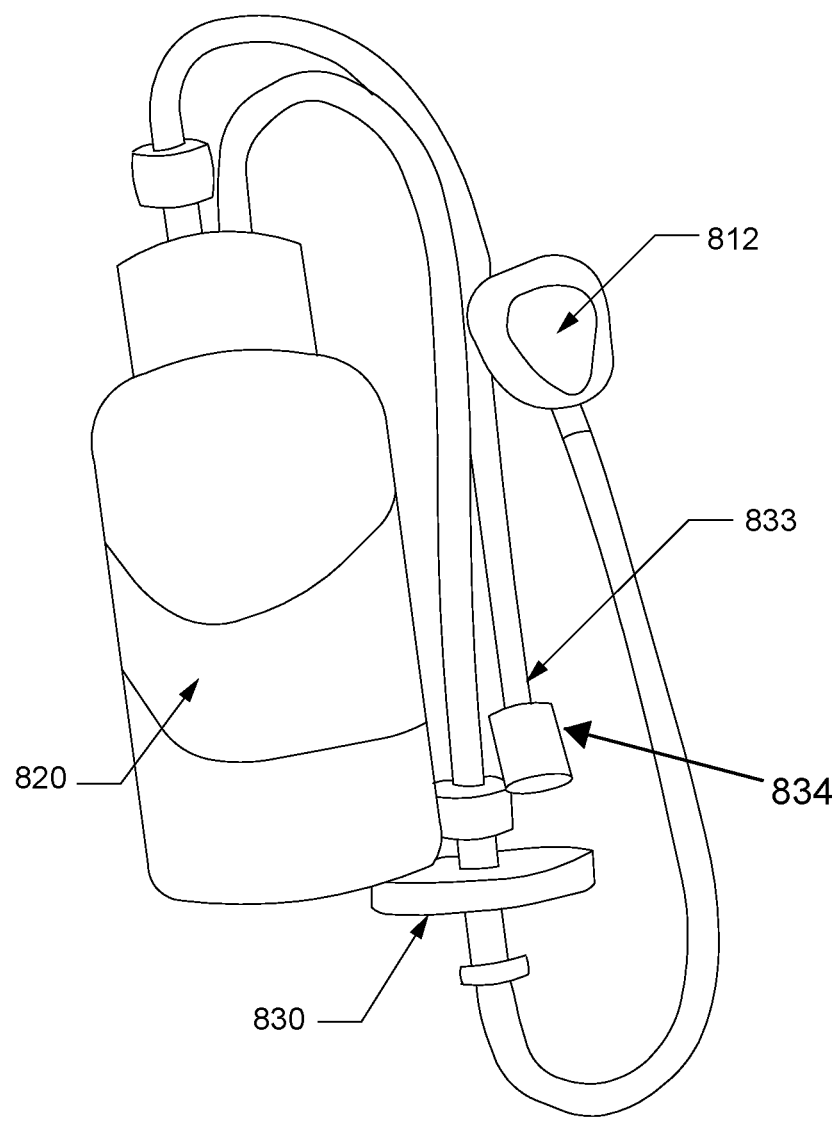
FIG. 8B shows another view of the fluid removal device.

FIG. 8B shows another view of the fluid removal device. FIG. 8B shows the activated carbon filter 820, the secondary filter 830, aspirator tube 833, patient contact device 834 is at the end of aspirator tube 833, and a connector 812. The connector 812 connects to pump 810, which is a vacuum pump.

Methods of Hollow Body Organ Ablation

Figure 9:
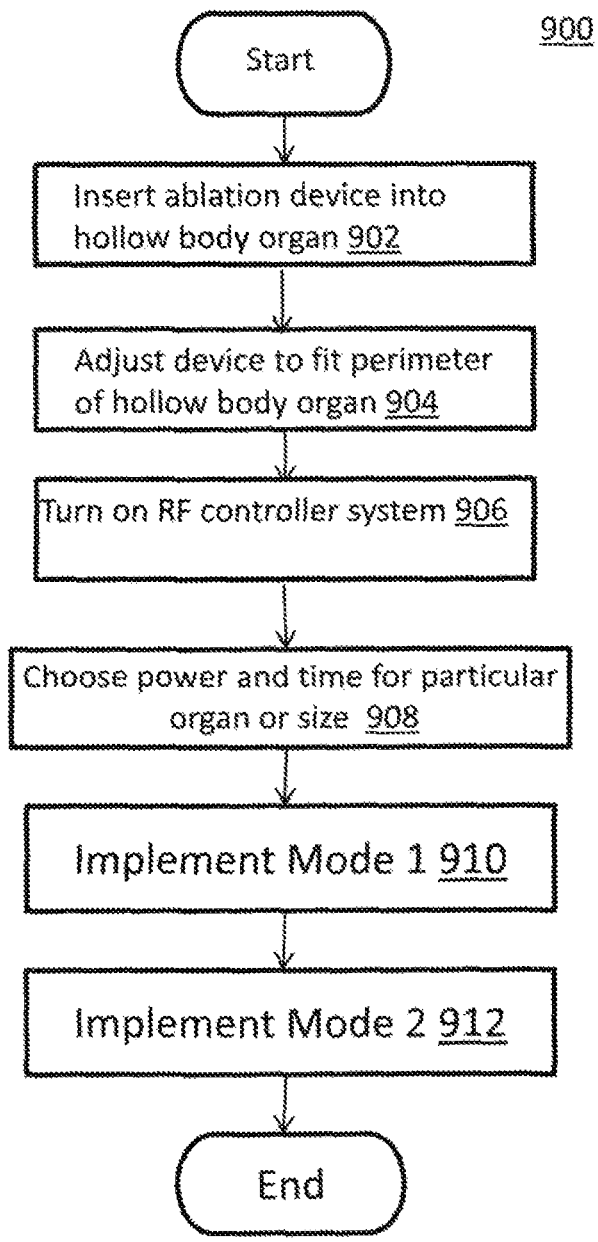
FIG. 9 shows a flowchart of a method of using an embodiment of a hollow body ablation device.

FIG. 9 shows a flow chart of an embodiment of method 900 in which a hollow body ablation apparatus (see 100 in FIG. 1A, for example) is used in a method of hollow body organ ablation.

Advantages of methods of using embodiments of the ablation devices include the ability to reduce the overall profile and size of the device to allow for minimally invasive access, to be able to better conform to organs with distorted cavity shapes, and to reduce the overall cost of manufacturing such devices. Ablation is defined as removal or excision. Ablation of the interior lining of a body organ is a procedure which involves heating the organ lining to temperatures which destroy the cells of the lining or coagulate tissue proteins for hemostasis.

Embodiments of ablation apparatus 100 may be used in cases where the hollow body cavity is more of a potential space (e.g., it is a hollow body cavity that might normally collapse down upon itself unless held open by some means). A good example of such a hollow body cavity would be the female human uterus. The uterine cavity is normally a small triangular shaped cavity with an entrance at the cervix. The cavity is basically flat, like an envelope, and is open only when filled with some material or possibly pressurized. Since the cavity is essentially flat, the anterior and posterior inner surfaces may or may not be in either partial or direct contact with each other, and a well defined perimeter exists. Whether the anterior and posterior surfaces are in contact with each other or not, the ablation is still effective and complete.

The methods involve inserting an ablation apparatus into a hollow body organ thru an aperture and ablating the interior lining of the organ.

In step 902 an ablation device such as those described in FIGS. 1-6 is inserted into a hollow body organ. The methods can be used for any hollow body organ, including but not limited to, a uterus, and a gall bladder. The device is inserted in the collapsed position to allow insertion through a small aperture into the organ. The efficient packing of right and left halves of the head of the hollow body ablation device when collapsed (folded up) prior to deployment, reduces the overall dimensions of the device for either insertion through a natural orifice, or through an incision. Reducing the size during deployment can be important for minimizing trauma to the patient or to reduce anesthesia requirements to control pain during insertion.

In step 904, the device is adjusted to fit the perimeter of the organ. A perimeter can be thought of as the length of the outline of a shape. For example, the size of a uterus can vary from patient to patient, but has an approximately triangular shape. Thus, the device can be adjusted to change the size of the triangular area to fit the shape and/or size of a particular uterus.

In step 906 the power controller is turned on, and the dimension of the region being ablated is input into the controller (the controller may be turned on earlier, but the power applied, algorithm chosen is based on the dimensions and/or characteristics of the cavity). In step 908 an algorithm, the amount of power, and duration of time that is power is applied, is automatically chosen for a particular organ, based on the organ, size, for example, based on a lookup table (e.g., according to lookup table 216). In some embodiments, the algorithm decides the type and amount of alternating current (AC) applied to the electrodes. The algorithm may include a determination of the frequency. In some embodiments, the amount and power are applied differently to different pairs of electrodes. Examples of some algorithms that can be used can be found in the description of FIG. 1D. In some embodiments steps 906 and 908 occur simultaneously. In some embodiments, the treatment algorithm may be read from a lookup table stored in a storage means within the ablation device, for example within an EEPROM, compact disk, microprocessor ROM, flash disk or other type of storage media or medium.

In some embodiments, in step 910, mode 1 is implemented (see FIG. 1D for a description of mode 1). A first amount of power is applied for a given period of time to a first region of the organ. The power may be applied by automatically applying a voltage, automatically measuring the current, and then automatically adjusting the voltage until the power output is at the desired level. In an embodiment, the process of finding the power level may be iterative.

In step 912, mode 2 is implemented (see FIG. 1D for a description of mode 2). A second amount of power that is different (e.g. lower) than the amount of power applied in step 910 is applied for a second period of time (e.g., a shorter period of time) to a second region of the organ (e.g., a region having a smaller distance between the walls at the perimeter of the organ. As in step 912, the power may be applied by automatically applying a voltage, automatically measuring the current, and then automatically adjusting the voltage until the power output is at the desired level. During steps 910 and 912, the amount of power used for the method can be from about 20 to about 100 W, including about 30, 40, 50, 60, 70, 80, and 90 watts. In some embodiments, the amount of power is between about 40 and about 50 W. The power can be left on for a time of between about 50 and about 300 seconds, including but not limited to, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 and all integers in between, depending on the organ an the dimensions of the organ. In some embodiments the power is left on for a time of between about 100 and about 150 seconds, depending on the organ the dimensions of the organ.

In an embodiment, each of the steps of method 900 is a distinct step. In another embodiment, although depicted as distinct steps in FIG. 9, step 902-912 may not be distinct steps. In other embodiments, method 900 may not have all of the above steps and/or may have other steps in addition to or instead of those listed above. The steps of method 900 may be performed in another order. Subsets of the steps listed above as part of method 900 may be used to form their own method.

Methods of Making Hollow Body Organ Ablation Devices

Figure 10:
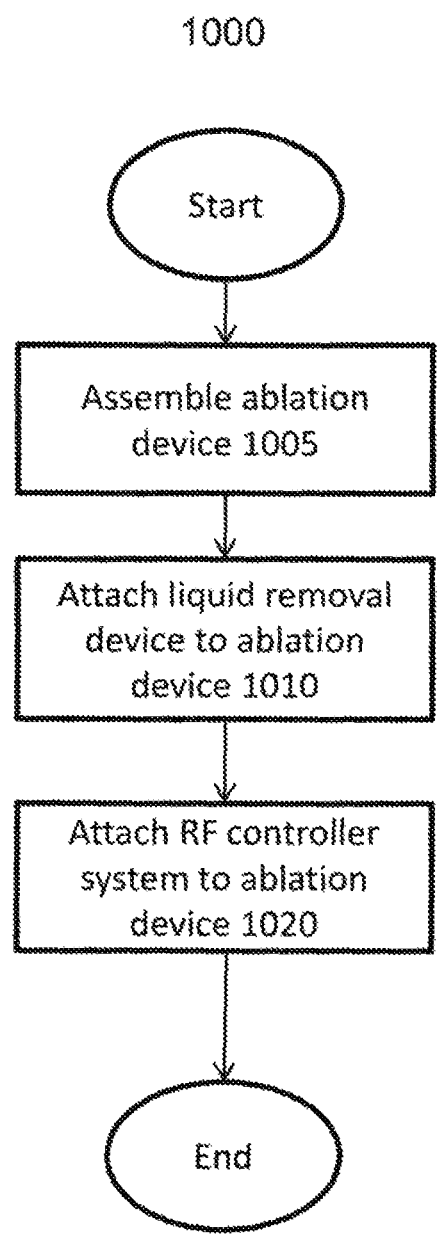
FIG. 10 shows a flowchart of a method of assembling the system components of an embodiment of a hollow body ablation apparatus.

FIG. 10 shows a flow chart of an embodiment of method 1000 in which a hollow body ablation apparatus (see 100 in FIG. 1A, for example) is configured.

In step 1005 the ablation device (see 101 in FIG. 1) is assembled. An embodiment of step 1005 is discussed in conjunction with FIG. 11.

In step 1010, a fluid removal device is attached to the ablation device (see 101 in FIG. 1). The fluid removal device can include a tube that can be snaked up through the handle and/or through the device to leave an opening within or next to the device. The tube can be attached to a reservoir and/or pump.

In step 1020 a controller is attached to the ablation device. The controller can also be attached to an electrical outlet and can control the amount of power the electrodes deliver to the tissue (by controlling the voltage applied to the electrodes) and/or the algorithm to be used. Thus, attaching the controller may include attaching the controller to the wires that are attached to the electrodes through a connector. The connector can be a wire with a plug having at least 6 pins, one pin for each electrode on head 110. Optionally, there may be an additional two or more pins, and a controller may be attached to the additional pins. Using the additional pins, the controller may also be used for recording information about the ablation, such as the power, and duration of time of each mode applied.

In an embodiment, each of the steps of method 1000 is a distinct step. In another embodiment, although depicted as distinct steps in FIG. 10, step 1002-1020 may not be distinct steps. In other embodiments, method 1000 may not have all of the above steps and/or may have other steps in addition to or instead of those listed above. The steps of method 1000 may be performed in another order. Subsets of the steps listed above as part of method 1000 may be used to form their own method.

Figure 11:
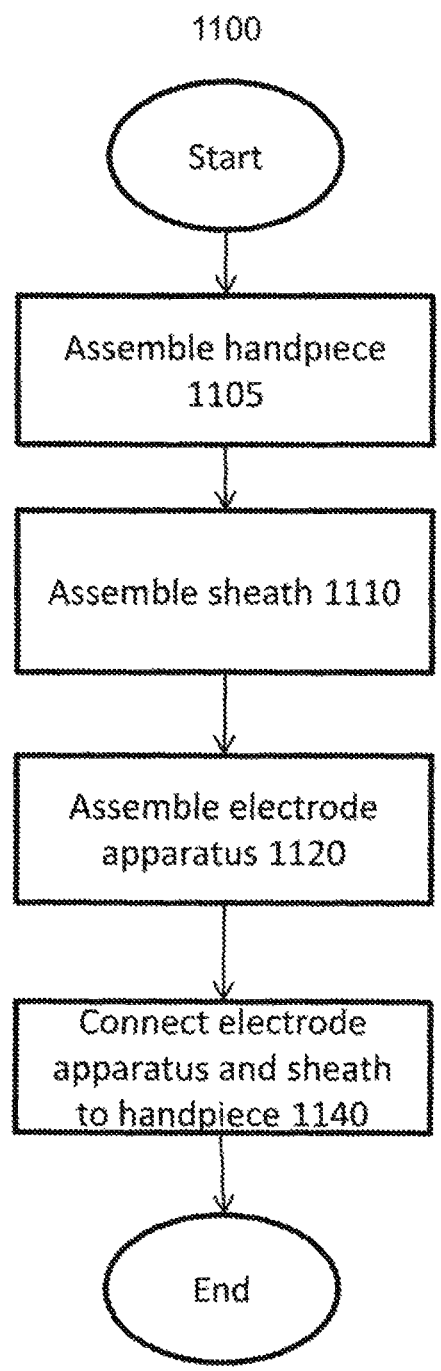
FIG. 11 shows a flowchart of a method of assembling the system components of the hollow body ablation device.

FIG. 11 shows a flow chart of an embodiment of method 1100 in which an ablation device (see 101 in FIG. 1A, for example) is configured. Method 1100 is an embodiment of step 1005 in FIG. 10.

In step 1105 a handpiece is assembled to include knobs for adjustment of the length and width of the device. The knobs can be attached to the central push/pull-wires 438 to control the collapsing of the electrode apparatus into the sheath. In some embodiments, within the handpiece the knobs are attached to levers which are attached to push and pull wires and moving the knobs moves the push and pull wires as needed to change the width and length of the device. The knobs can move the levers by sliding the levers along a groove (e.g., in a side to side direction to change the width and/or in a back to front direction to change the length). In some embodiment, the knobs can be attached to a lever that is attached to a push or pull wire that moves the sheath up or down as desired for insertion of the device.

Within the handpiece are wires connecting electrodes to the power source and/or controller. In some embodiments, there are the same number of wires as electrodes. The wires can be connected to the controller via a power cord and plug. Also included within the handpiece is an aspirator tube to allow removal of fluid during the procedure.

In step 1110 a sheath is assembled by attaching the sheath to the handpiece and to a width and/or length adjustment knob on the handpiece. The adjustment knob can be attached to a push or pull wire that pushes or pulls the sheath over the device or back from the device depending on the way the knob is turned or moved.

In step 1120 the head (e.g., the electrode apparatus) is assembled to be the approximate shape of the hollow body organ (e.g., triangularly shaped, a parallelogram or oval). The head has electrodes on the base and the sides of the device. Each side of the device is attached so that the sheath can be moved to cover the electrodes. The electrodes are chosen to allow movement into and out of the sheath. The electrodes are chosen to allow movement of the device from a triangular shape (or parallelogram) to two parallel sides covered by the sheath when collapsed. The electrodes can include moveable electrodes and rigid electrodes. The electrodes can include D-shaped electrodes to allow the device to be collapsible. The electrodes can be separated by insulators to keep the electrodes from touching.

In step 1140 the electrode apparatus, sheath and handpiece are attached so that a user can manipulate the device to collapse and cover the electrode apparatus (e.g., with the sheath) so that when inserted the device can fit through a small aperture. This step also allows the user to manipulate the length and width of the device to fit the size of the hollow body organ.

In an embodiment, each of the steps of method 1100 is a distinct step. In another embodiment, although depicted as distinct steps in FIG. 11, step 1105-1140 may not be distinct steps. In other embodiments, method 1100 may not have all of the above steps and/or may have other steps in addition to or instead of those listed above. The steps of method 1100 may be performed in another order. Subsets of the steps listed above as part of method 1100 may be used to form their own method.

EXAMPLES

In the following examples, embodiments of the ablation devices were used to treat a test specimen (a beef steak) and the width, length and depth of treating was measured. Beef steak was used to approximate the hollow body organ—"a meat cavity." Using the methods and devices herein in which radio frequency electrodes were arranged in a pattern that made contact with the surface area of the beef steak, energizing the electrodes resulted in treatment of a much larger area than was specifically contacted by the electrodes. When used in a hollow body organ, this would result in a complete ablation of the lining of the body cavity, even though the electrodes only make contact with the surface area of the organ in proximity to the perimeter. This has numerous advantages over the prior art in which devices to perform complete ablation of a hollow body cavity required that radio frequency electrodes cover all or substantially all of the surface area to be ablated, rather than just a portion of the surface area in close proximity to the perimeter of the organ.

Example 1: Test Treatment of a Beef Steak with the Ablation Device Shown in FIG. 1

Example 1 describes the results from a test for the endometrial ablation device shown in FIG. 1A. The tests assumed a uterus size of 4.5 cm wide by 6.5 cm long. Thus, the device was configured to have a 4.5 cm long base and 6.5 cm long sides. All tests were performed using two slices of beef in a "meat cavity".

Figure 12:
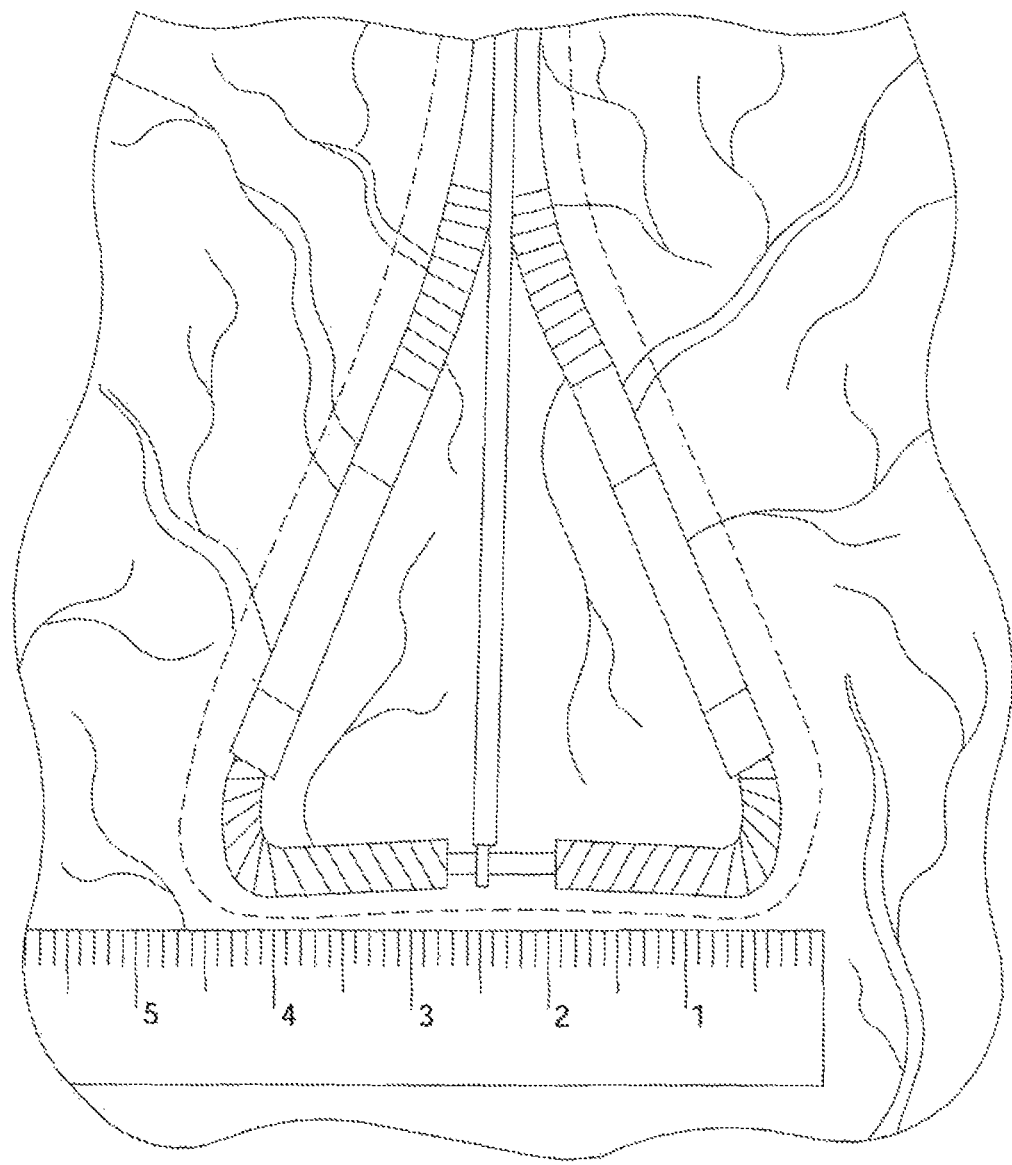
FIG. 12 shows a front elevation view of a method of testing a hollow body ablation apparatus post treatment.
Figure 13:
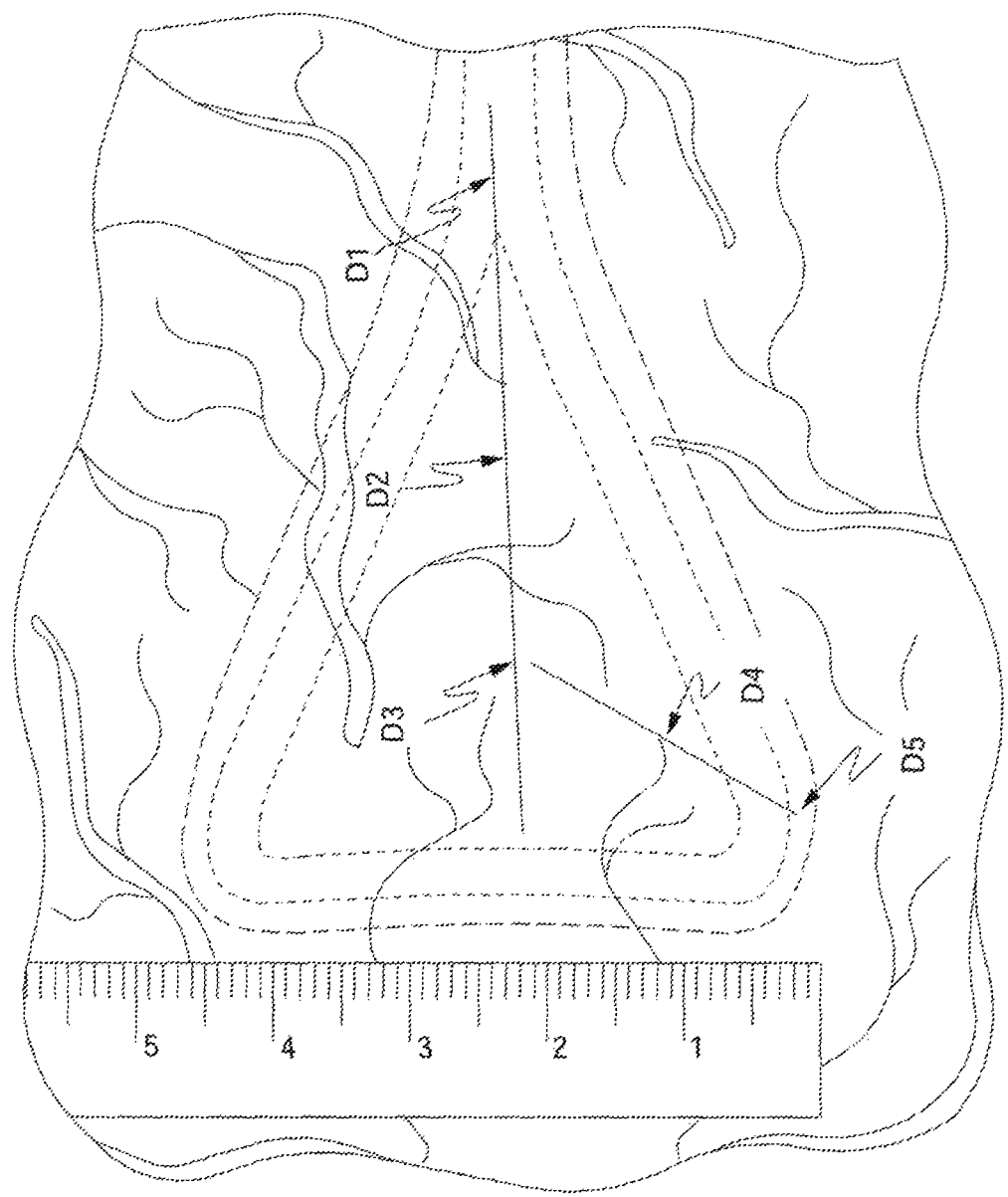
FIG. 13 shows a front elevation view of a method of testing a hollow body ablation apparatus post treatment.
Figure 14:
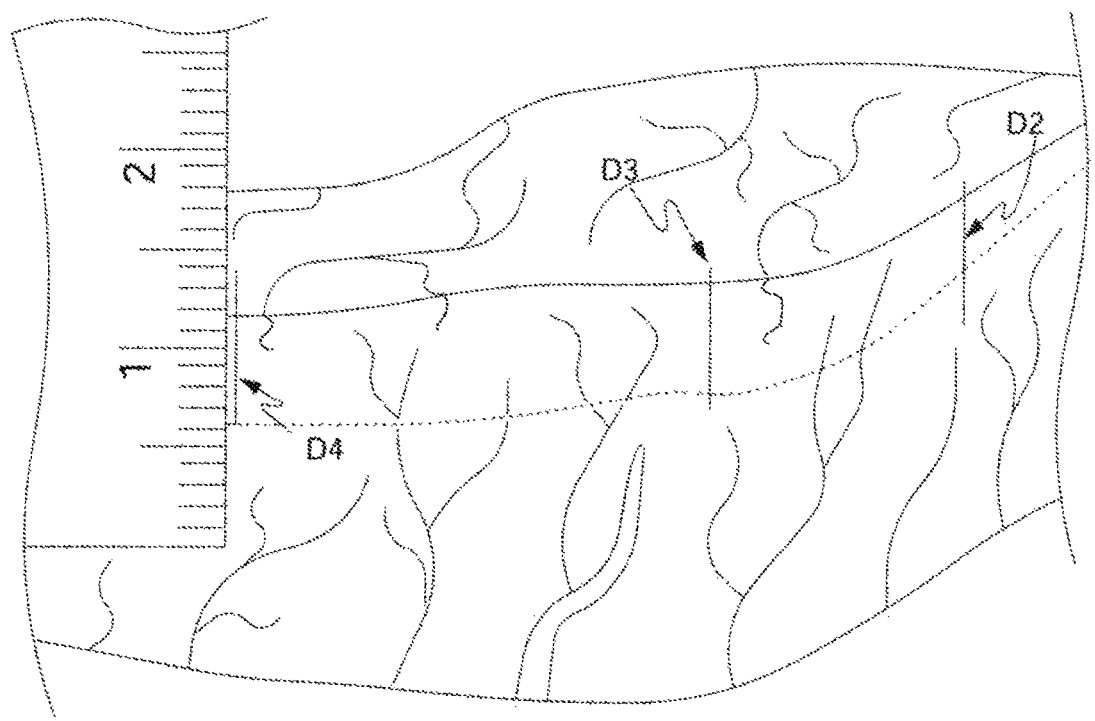
FIGS. 14 and 15 show side elevations of the ablated test material.
Figure 15:
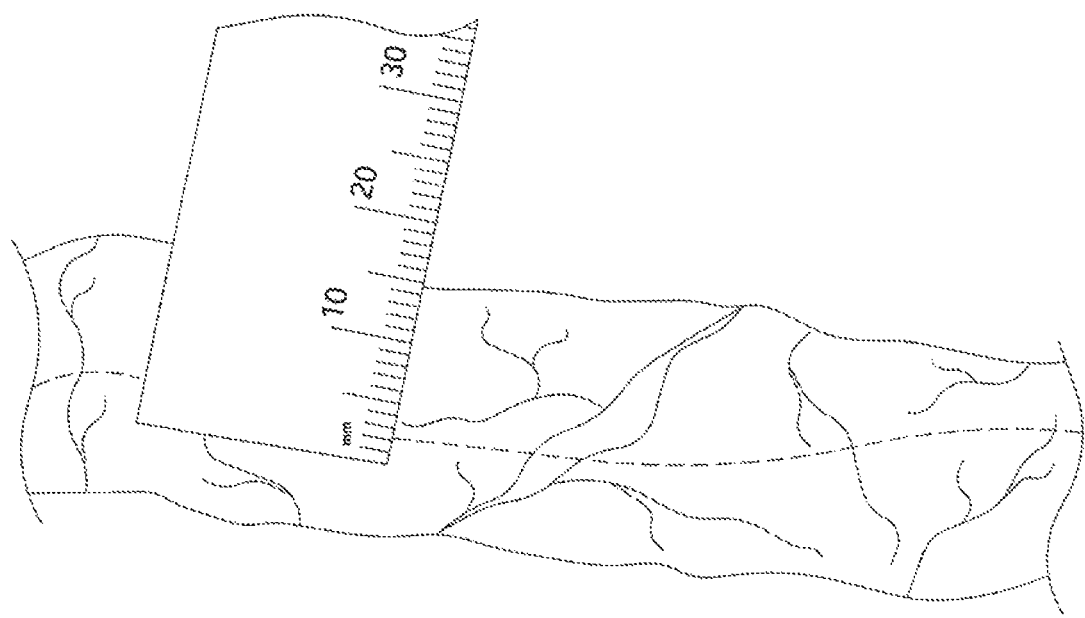

As shown in FIGS. 12 and 13, the device was configured with six electrode segments as follows: The distal electrodes (on the base) were 0.077" diameter, stainless steel extension springs. The middle electrodes were stainless steel D-tubing created from 3.75 mm OD tubing (9 GA). The D-length was 2.60 mm and the D-width was 4.55 mm. The proximal electrodes were stainless steel D-tubing (as above) with slots cut in the round portion of the D to allow for flexibility in only one plane. The goal of the test was to find the optimum power and time settings to effectively treat the tissue. So, a number of tests were performed varying the amount of power (watts), the amount of time (seconds) and using more than one mode as follows:

Test 1. FIG. 12 shows a front elevation view of the method of testing a hollow body ablation apparatus in which RF energy was applied at 50 W for 120 seconds for mode 1. In FIG. 13 the RF had not yet been applied to the electrodes, but the head of the device was fully opened. FIG. 12 shows a front elevation view of the method of testing a hollow body ablation apparatus—after applying mode 1 at 50 Watts for 120 seconds. FIG. 12 shows that the electrodes affected an area wider than the width of the electrodes. In fact, the whole area defined by the head of the device was affected including up to 10 mm outside of the electrodes. Thus, as judged by the widely affected area, the algorithm does more than just apply current.

FIG. 13 shows a front elevation view of a method of testing a hollow body ablation apparatus—post-treatment without the device. FIG. 13 shows that the treatment affected the area within the devices electrodes and also an area of between 3 and 10 mm outside of the area that the electrodes touched. The amount of heating was surprisingly even, although there was more heating directly under the electrodes.

The depth of the treatment was analyzed by cutting the steak through the centerline and sides of the affected area and measuring the depth. The steak was affected at a depth of about 4 to 10 mm at the centerline of the treatment as well as directly under the electrodes. FIG. 13 also shows test points D1-D5 at which the depth of ablation is measured. The test area is cut along the lines connecting points D1-D5 so that the depth of heating can be measured.

Other tests were as follows:

Test 2: Mode 1 was 40 watts for 150 seconds; Mode 2 was 30 watts for 30 seconds. This method showed an equal effectiveness to the first test.

Test 3: Mode 1 was 50 watts for 113 seconds. This method showed an equal effectiveness to the first test.

Test 4: Mode 1 was 40 watts for 150 seconds; Mode 2 was 30 watts for 30 seconds. This method showed an equal effectiveness to the first test.

The smaller overall surface area of the smaller round springs resulted in a higher energy density at similar powers. To get the desired results, settings of 40 W for 150 seconds and 30 W for 30 seconds was required. However, higher powers resulted in charring and therefore less effective treatment time.

Table 2 provides the results for 20 different treatments using different widths and lengths, and a variety of modes. In Tables 2A and 2B, FIGS. 16 and 17, depth is provided for electrodes D1-D6. The numbering of the electrodes is as shown in FIG. 1A2. However, in all cases, the depth of treatment as shown resulted in a good result. The test results were unexpectedly good in that the periphery (which is close to or in contact with the electrodes) is not charred, the entire cavity is heated (including the central area in the center of the opening of the head 110), and the depth of heating is shallow enough so as not to heat the myometrium or serosal layer of the uterus.

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A hollow body ablation apparatus, comprising:
a head having at least three electrodes, at least one insulator, the head comprising an elongated member having sides and a base, the sides and the base being flexible, wherein the sides have a length and the base has a width;
a sheath;
a handpiece connected to the head including at least
a width adjustment and
a length adjustment
when the width adjustment is activated, the width adjustment adjusts the width of the base of the head and when the length adjustment is activated, the length adjustment adjusts the length of the sides of the head, wherein the head can be collapsed into the sheath using the length adjustment;
a controller in electrical communication with the at least three electrodes, the controller having modes, which, when activated, causes the controller to energize the at least three electrodes, the controller having a bipolar mode of operation, which, when activated while in contact with tissue, causes electrical fields to be established in tissue within a perimeter outlined by the at least three electrodes, and when the bipolar mode is activated the electrical fields ablate the tissue within all of the perimeter while not heating a myometrium.

2. The hollow body ablation apparatus of claim 1, wherein at least one electrode of the at least three electrodes is flexible.

3. The hollow body ablation apparatus of claim 1, wherein the at least one insulator is flexible.

4. The hollow body ablation apparatus of claim 1, wherein at least one of the at least three electrodes is a coil electrode.

5. The hollow body ablation apparatus of claim 1, wherein at least one electrode of the at least three electrodes is a tube electrode, the tube electrode having a cross sectional shape that is noncircular.

6. The hollow body ablation apparatus of claim 1, wherein at least two electrodes of the at least three electrodes are slotted and each includes at least a tube having a D-shaped cross section having a flat side, wherein, when in use, the flat side of each D-shaped cross section is perpendicular to the tissue being ablated, wherein the flat sides of each D-shaped cross section face each other when the head is collapsed.

7. The hollow body ablation apparatus of claim 1, wherein the at least three electrodes includes at least a conductive bead-chain.

8. The hollow body ablation apparatus of claim 1, wherein the at least three electrodes has at least an accordion structure, so as to be foldable in a manner of an accordion.

9. The hollow body ablation apparatus of claim 1, wherein the at least three electrodes includes at least a braided metallic wire.

10. The hollow body ablation apparatus of claim 1, wherein the at least three electrodes has a telescopic structure.

11. The hollow body ablation apparatus of claim 1, wherein the sheath has a cross section with a diameter between about 4 and 6.5 mm.

12. The hollow body ablation apparatus of claim 1, wherein, the at least three electrodes comprise at least two D-type electrodes, the at least two D-type electrodes including at least a tubular electrode with a "D" shape cross section having a rounded side and a flat side, wherein the flat side of one of the at least two D-type electrodes faces the flat side of another of the at least two D-type electrodes.

13. The hollow body ablation apparatus of claim 1, wherein the width adjustment is adjacent to a width scale, which indicates how much the width is exposed, and
wherein the length adjustment is adjacent to a length scale, which indicates how much the length is exposed.

14. The hollow body ablation apparatus of claim 1, wherein the head has a triangular shape, and at least one of the at least three electrodes is a preloaded spring, which tends to push the head into the triangular shape.

15. A hollow body ablation apparatus, comprising:
a handpiece;
a head having an end that is distal from the handpiece and two sides, the two sides having a section that is proximal to the handpiece, the head having at least six electrodes, wherein two electrodes of the at least six electrodes are located on the end, and four electrodes of the at least six electrodes are located on the two sides, the end and the two sides defining a perimeter of the head;
at least one insulator;
a sheath;
a width adjustment and a length adjustment, wherein the width adjustment and the length adjustment operate separately, wherein when the width adjustment is activated, the width adjustment adjusts how far apart the ends of the sides that are distal from the hand piece are from one another, wherein when the length adjustment is activated the length adjustment adjusts how much of the two sides are exposed and how much of the sides are covered by the sheath, wherein the width and length adjustments control a size of the perimeter of the head;
a controller having at least two modes of operation that are used for ablation of the hollow body, each of the at least two modes having different parameters;
and
wherein each of the at least six electrodes can be separately activated, such that the two electrodes of the at least six electrodes that are located on the end and a first pair of electrodes of the four electrodes that are located on the sides are activated during a first mode of the at least two modes and the second pair of the four electrodes is activated during a second mode of operation of the at least two modes.

16. The hollow body ablation apparatus of claim 15, wherein each of the at least six electrodes can be separately activated via applying an AC or radiofrequency (RF) energy delivery mode.

17. The hollow body ablation apparatus of claim 15, wherein the four electrodes of the at least six electrodes located on the two sides are placed as follows:
a first set of two electrodes of the four electrodes are located distal to the hand piece; and
a second set of two electrodes of the four electrodes are located on the section of the two sides that is proximal to the handpiece, and wherein the second set of two electrodes of the four electrodes can be activated separately from the first set of two electrodes.

18. The hollow body ablation apparatus of claim 15, further comprising at least one wire for at least one of the at least six electrodes connected through the sheath to the handpiece, wherein the at least one wire connects the at least one of the at least six electrodes to a power supply.

19. The hollow body ablation device of claim 15, each of the two sides and the base have at least one portion that remains flat as the head opens, so that the perimeter of the head, and the two sides has a straight portion extending along a length of each of the sides and so that the perimeter has a straight portion extending along a length of the base.

20. A hollow body ablation apparatus, comprising:
a head having at least three electrodes, at least one insulator, the head comprising an elongated member having sides and a base, the sides and the base being flexible, wherein the sides have a length and the base has a width;
a sheath;
a handpiece connected to the head including at least a width adjustment and a length adjustment that can adjust the width of the base and the length of the sides of the head, wherein the head can be collapsed into the sheath using the width or length adjustment;
a controller in electrical communication with the at least three electrodes, when the controller is activated, the controller controls at least two modes of energizing the at least three electrodes, the controller has a bipolar mode of operation, which when activated while in contact with tissue, causes electrical fields to be established in the tissue within a perimeter outlined by the at least three electrodes, when in the bipolar mode and while in contact with the tissue, the electrical fields ablate the tissue within all of the perimeter, by at least applying a first electrical field to only a first portion of the tissue within the perimeter while in a first mode of the at least two modes, and applying a second electrical field to only a second portion of the tissue within the perimeter while in a second mode of the at least two modes, the first portion and the second portion being different portions of the tissue within all the perimeter;
wherein the at least two sides and the base form a triangular shape when in a deployed configuration, wherein the width and length adjustments control a size of a perimeter of the head when deployed.

21. The hollow body ablation apparatus of claim 20, a perimeter outlining a region that has no electrodes within the region.

22. The hollow body ablation apparatus of claim 20, a perimeter outlining a region that has no components of the head within a central portion of the region.

23. The hollow body ablation device of claim 20, wherein the at least three electrodes includes at least six electrodes, and wherein the controller is in electrical communication with the at least six electrodes the controller having modes, which, when activated, causes the controller to energize the at least six electrodes, wherein, the controller is configured to detect a length and a width of the head.

24. The hollow body ablation device of claim 23, wherein the controller is configured to automatically determine parameters of an ablation mode based on the width and the length of the head.

25. The hollow body ablation device of claim 24, wherein the controller is configured to automatically determine an amount of power and time of application of the bipolar mode based on the width and the length of the head.

26. A hollow body ablation apparatus, comprising:
a head having
at least three electrodes, and
at least one insulator,
the head including an elongated member having sides and a base, the sides and the base having flexible portions, so that the head opens and closes, each side of the sides having a portion that is not flexible and the portion that is not flexible remains straight along a direction that is a direction of a length of each side of the sides as the head opens and closes, so that a perimeter of the head has a straight portion on each side, as the head opens and closes, so as to aid a perimeter of the head to achieve a predetermined shape, for a given length and width;
wherein the sides have a length and the base has a width;
each side having at least one of the at least three electrodes;
a sheath;
a handpiece connected to the head, the base of the head being further from the handpiece than the sides of the head;
a width adjustment;
a length adjustment; and
wherein when the length adjustment is activated to make the head shorter, the head collapses into the sheath, wherein the width adjustment and the length adjustment are separately operable.

27. The hollow body ablation apparatus of claim 26, the width adjustment comprising:
a width knob on an outside of the handpiece;
a width sliding member;
at least one lever;
at least one push-pull wire;
wherein the width knob is attached to the width sliding member and the width sliding member is further connected to the at least one lever, wherein the at least one lever is attached to the at least one push-pull wire which when pushed and when pulled adjusts the width of the base of the head.

28. The hollow body ablation apparatus of claim 26, the length adjustment comprising:
a length knob on an outside of the handpiece and
a length sliding member; and
wherein the length knob is attached to the length sliding member and the length sliding member is further connected to the sheath, wherein moving the length knob in a first direction slides the sheath up the handpiece to adjust a length of the sides of the adjustable head and moving the length knob in a second direction slides the sheath down the handpiece to adjust the length of the sides of the head.

29. A hollow body ablation apparatus, comprising:
a head having at least
a plurality of electrodes, and
at least one insulator,
the head including at least an elongated member having sides and a base, wherein each side has a length and the base has a length, the length of the base extending along a width of the head, the plurality of electrodes being arranged on the sides and base, the sides having internal axes, wherein each side has an internal axis extending along the length and the base having an internal axis extending along the length of the base and therein extending along the width of the head, and the sides and the base are arranged so that the internal axes of the sides and the internal axis of the base forms a single two dimensional shape, wherein at least two electrodes of the plurality of electrodes each includes at least a tube having a D-shaped cross section having a flat side, wherein, when in use, the flat side is perpendicular to a tissue being ablated, wherein when the head is collapsed the at least two electrodes each have the flat side of the D-shaped cross section facing one another;
a sheath;
a handpiece connected to the head including at least
a width adjustment, which, when activated, adjusts the width of the base;
a width indication that indicates a measure of the width of the base;
a length adjustment, which when activated, adjusts the length of the head;
a length indication that indicates a measure of the length of the base;
wherein when the length adjustment is adjusted beyond a particular amount in one of two directions, the head is caused to collapse into the sheath.

30. The hollow body ablation apparatus of claim 29, wherein the plurality of electrodes includes at least one rigid electrode.

31. The hollow body ablation apparatus of claim 29, wherein the sheath has a cross section with a diameter of 6.5 mm or less.

32. A hollow body ablation apparatus, comprising:
a handpiece;
a head having an end that is distal from the handpiece and two sides, the two sides having a section that is proximal to the handpiece, the head having at least six electrodes, wherein two electrodes of the at least six electrodes are located on the end, and four electrodes of the at least six electrodes are located on the two sides, the end and the two sides defining a perimeter of the head;
at least one insulator;
a sheath;
a width adjustment and a length adjustment, wherein the width adjustment and the length adjustment operate separately, wherein when the width adjustment is activated, the width adjustment adjusts how far apart ends of the sides that are distal from the hand piece are from one another, wherein when the length adjustment is activated, the length adjustment adjusts how much of the two sides are exposed and how much of the two sides are covered by the sheath; and
wherein each of the at least six electrodes can be separately activated; and
a controller having two predefined modes of operation;
in a first mode of the two modes, the two electrodes located on the and the two electrodes located on the two sides that are closest to the end are activated to form a first set of electric fields traversing a region within the perimeter at the end of the head furthest from the handpiece; and
in a second mode of the two modes, two electrodes on opposite sides of the head that are furthest from the end are activated to have opposite charges, forming a second set of electric fields traversing a remainder of the region within the perimeter of the head.

33. The hollow body ablation apparatus of claim 32, wherein the controller is configured such that when the controller is activated in the first mode, the two electrodes located on the two sides that are closest to the base participating in the first mode have opposite polarities and the two electrodes located on the base have opposite polarities.

34. The hollow body ablation apparatus of claim 32, wherein the controller is configured such that the first mode applies between 58 and 82 Watts for between 60 and a 120 seconds in association with generating the first set of electric fields.

35. The hollow body ablation apparatus of claim 34, the region within the perimeter of the head having a length of between 3.5 cm and 7 cm and a width of 1.5 cm and 5 cm.

36. The hollow body ablation apparatus of claim 34, wherein the controller is configured such that the second mode applies between 18 and 42 Watts in association with generating the second set of electric fields.

37. A hollow body ablation apparatus, comprising:
a head having
at least three electrodes, and
at least one insulator,
the head including an elongated member having sides and a base, the sides and the base being flexible, each side having a portion that remains flat as the head opens and closes;
wherein the sides have a length and the base has a width;

each side having at least one of the at least three electrodes;
a sheath;
a handpiece connected to the head, the base of the head being further from the handpiece than the sides of the head;
a width adjustment;
a length adjustment; and
wherein when the length adjustment is activated to make the head shorter, the head collapses into the sheath,
wherein the width adjustment and the length adjustment are separately operable, wherein
  the sides being attached to the base by flexible regions that bend more than the sides, and the base having a portion with an electrode that remains flat while the flexible regions bend, the electrode that remains flat being one of the at least three electrode;
  a first of the flexible regions distinctively demarking a separation between a first of the sides and the base; and
  a second of the flexible regions distinctively demarking a separation between a second of the sides and the base.

\* \* \* \* \*